United States Patent
Badescu et al.

(10) Patent No.: US 7,910,588 B2
(45) Date of Patent: Mar. 22, 2011

(54) 5-HT7 RECEPTOR ANTAGONISTS

(75) Inventors: Valentina O Badescu, Fishers, IN (US);
Sandra Ann Filla, Franklin, IN (US);
Peter Thaddeus Gallagher, Hampshire (GB); Maria Ann Whatton, Bracknell (GB)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 12/678,345

(22) PCT Filed: Sep. 30, 2008

(86) PCT No.: PCT/US2008/078294
§ 371 (c)(1),
(2), (4) Date: Mar. 16, 2010

(87) PCT Pub. No.: WO2009/048765
PCT Pub. Date: Apr. 16, 2009

(65) Prior Publication Data
US 2010/0197700 A1    Aug. 5, 2010

Related U.S. Application Data

(60) Provisional application No. 60/979,464, filed on Oct. 12, 2007.

(51) Int. Cl.
*A61K 31/444* (2006.01)
*A61K 31/497* (2006.01)
*C07D 401/14* (2006.01)
*C07D 403/14* (2006.01)

(52) U.S. Cl. .............. 514/252.11; 514/253.09; 544/357; 544/364

(58) Field of Classification Search ................. None
See application file for complete search history.

(56) References Cited

U.S. PATENT DOCUMENTS 6,465,467 B1    10/2002    Nilsson et al.

FOREIGN PATENT DOCUMENTS

| EP | 1254905 B1 | 12/2003 |
|---|---|---|
| WO | 2004/067703 A2 | 8/2004 |
| WO | 2005/069794 A2 | 8/2004 |
| WO | 2005/117883 A1 | 12/2005 |

OTHER PUBLICATIONS

Lepailleur, et al. J. Chem. Inf. Model 2005, 45, 1075-1081 Molecular Modeling Studies Focused on 5-HT7 versus 5-HT1A Selectivity. Discovery of Novel Phenylpyrrole Derivatives with High Affinity for 5-HT7 Receptors.
Terron J., European Journal of Pharmacology, 2002, 439, 1-11 "Is the 5-HT7 receptor involved in the pathogenesis and prophylactic treatment of migraine?".
Hedlund, et al., Trends in Pharmacological Sciences, vol. 25, 9, 2004, "Functional, molecular and pharmacological advances in 5-HT7 receptor research".
M. Leopoldo., Current Medicinal Chemistry, 11, 629-661, 2004, Serotonin7 Receptors (5-HT7Rs) and their Ligands.

*Primary Examiner* — Emily Bernhardt
(74) *Attorney, Agent, or Firm* — R. Craig Tucker

(57) ABSTRACT

The present invention provides selective 5-HT$_7$ receptor antagonist compounds of Formula I and their use in the treatment of migraine:

where A is —C(H)= or —N= and $R^{1-7}$ are as defined herein.

7 Claims, No Drawings

5-HT7 RECEPTOR ANTAGONISTS

The neurotransmitter serotonin (5-hydroxytryptamine, 5-HT) has a rich pharmacology arising from a heterogeneous population of at least 14 distinct receptors. Each receptor has a distinct, though often overlapping distribution throughout the body and a unique serotonin binding site leading to different affinities for serotonin and different physiological responses to interaction with serotonin. The $5\text{-HT}_7$ receptor has been shown to have important functional roles in thermoregulation, circadian rhythm, learning and memory, hippocampal signaling, and sleep. The $5\text{-HT}_7$ receptor has also been linked to various neurological disorders including migraine and anxiety, as well as to persistent pain, more specifically inflammatory pain and neuropathic pain.

High affinity $5\text{-HT}_7$ receptor antagonists would provide useful therapeutics for the treatment of the above mentioned $5\text{-HT}_7$ receptor-associated disorders including migraine, and persistent pain, particularly, inflammatory and neuropathic pain. High affinity $5\text{-HT}_7$ receptor antagonists that are also selective for the $5\text{-HT}_7$ receptor would provide such therapeutic benefit without the undesirable adverse events associated with modulation of the other receptor types, as for example the other serotonergic receptor subclasses, such as $5\text{-HT}_{1A}$, $5\text{-HT}_{1B}$ and $5\text{-HT}_{1D}$ or alpha adrenergic receptors. Achieving selectivity for the $5\text{-HT}_7$ receptor over other 5-HT receptor subtypes has proven difficult in designing $5\text{-HT}_7$ antagonists. $5\text{-HT}_{1A}$ receptor agonists have been associated with serotonin syndrome. $5\text{-HT}_{1B}$ and $5\text{-HT}_{1D}$ receptor agonists have been associated with adverse events such as chest pain.

Leopoldo, M. (2004) "Serotonin(7) receptors (5-HT(7)Rs) and their ligands" Curr. Med. Chem. 11, 629-661, describes various prior approaches to obtaining $5\text{-HT}_7$ receptor ligands. WO 2004/067703 describes $5\text{-HT}_7$ antagonists including certain 2-(piperazin-1-yl)-3-phenyl-pyrazines and pyridines.

The present invention provides novel potent $5\text{-HT}_7$ receptor antagonists. Certain compounds of the present invention are selective for the $5\text{-HT}_7$ receptor compared with other serotonin receptors.

The present invention provides selective $5\text{-HT}_7$ receptor antagonist compounds of Formula I:

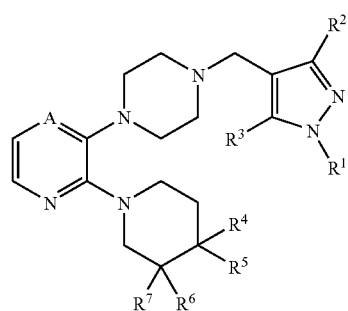

where:
A is —C(H)═ or —N═,
$R^1$ is a substituent selected from the group consisting of i) hydrogen, ii) methyl, iii) ethyl, iv) hydroxymethyl, v) hydroxyethyl, vi) phenyl optionally substituted with 1 to 3 fluoro groups, vii) benzyl optionally substituted with 1 to 3 fluoro groups, and viii) pyridyl;
$R^2$ is hydrogen, methyl, or ethyl;
$R^3$ is hydrogen, methyl, or chloro;
$R^4$ is selected from the group consisting of i) hydrogen, ii) fluoro, iii) methyl, iv) hydroxy, v) hydroxymethyl, vi) hydroxyethyl, vii) methoxymethyl, viii) cyanomethyl, and ix) methylsulfonylaminomethyl;
$R^5$ is hydrogen or fluoro, provided that when $R^5$ is fluoro, $R^4$ is fluoro;
$R^6$ and $R^7$ are the same and are selected together from the group consisting of hydrogen, methyl, and fluoro, provided that when $R^6$ and $R^7$ are not hydrogen, $R^4$ and $R^5$ are both hydrogen;
or a pharmaceutically acceptable salt thereof.

The present invention also provides pharmaceutical compositions comprising a compound of Formula I, or a pharmaceutically acceptable salt thereof, in association with a pharmaceutically acceptable carrier, diluent, or excipient.

In another aspect of the present invention, there is provided one or more compounds of Formula I, or pharmaceutically acceptable salt(s) thereof for use in therapy. This aspect includes one or more compounds of Formula I, or pharmaceutically acceptable salt(s) thereof for use as a pharmaceutical. Likewise, this aspect of the invention provides one or more compounds of Formula I, or pharmaceutically acceptable salt(s) thereof for use in the treatment of migraine in mammals, particularly humans, the prophylactic treatment of migraine in mammals, particularly humans, and/or the treatment of persistent pain, particularly inflammatory or neuropathic pain, in mammals, particularly humans.

One embodiment of this aspect of the invention provides a method for treating migraine in mammals comprising administering to a mammal in need of such treatment an effective amount of a compound of Formula I, or a pharmaceutically acceptable salt thereof.

Another embodiment of this aspect of the invention provides a method for the prophylactic treatment of migraine in mammals comprising administering to a mammal in need of such treatment, that is to say a mammal that is susceptible to migraine, an effective amount of a compound of Formula I, or a pharmaceutically acceptable salt thereof.

Yet another embodiment of this aspect of the invention provides a method for the treatment of persistent pain in mammals comprising administering to a mammal in need of such treatment an effective amount of a compound of Formula I, or a pharmaceutically acceptable salt thereof. Particular embodiments of this are the treatment of inflammatory pain and/or neuropathic pain.

Yet another embodiment of this aspect of the invention provides a method for treating anxiety in mammals comprising administering to a mammal in need of such treatment an effective amount of a compound of Formula I, or a pharmaceutically acceptable salt thereof.

In preferred embodiments of the above methods of treatment utilizing the compounds of Formula I, or pharmaceutically acceptable salts thereof, the mammal is a human.

In another aspect of the present invention, there is provided the use of a compound of Formula I, or pharmaceutically acceptable salt thereof, in the manufacture of a medicament for the treatment and/or the prophylactic treatment of migraine.

In another aspect of the present invention, there is provided the use of a compound of Formula I, or pharmaceutically acceptable salt thereof, in the manufacture of a medicament for the treatment of persistent pain, particularly inflammatory and/or neuropathic pain.

In another aspect of the present invention, there is provided the use of a compound of Formula I, or pharmaceutically acceptable salt thereof, in the manufacture of a medicament for the treatment of anxiety.

Additionally, the present invention provides a pharmaceutical formulation adapted for the treatment of migraine and/or for the prophylactic treatment of migraine, comprising a compound of Formula I, or a pharmaceutically acceptable salt thereof, in association with a pharmaceutically acceptable carrier, diluent or excipient.

Likewise, the present invention provides a pharmaceutical formulation adapted for the treatment of persistent pain, particularly inflammatory and/or neuropathic pain, comprising a compound of Formula I, or a pharmaceutically acceptable salt thereof, in association with a pharmaceutically acceptable carrier, diluent or excipient.

Additionally, the present invention provides a pharmaceutical formulation adapted for the treatment of anxiety comprising a compound of Formula I, or a pharmaceutically acceptable salt thereof, in association with a pharmaceutically acceptable carrier, diluent or excipient.

The general chemical terms used throughout have their usual meanings.

The term "amino protecting group" as used in this specification refers to a substituent commonly employed to block or protect an amino functionality while reacting other functional groups on the compound. The species of amino protecting group employed is not critical so long as the derivatized amino group is stable to the conditions of subsequent reactions on other positions of the molecule and can be removed at the appropriate point without disrupting the remainder of the molecule. The selection and use (addition and subsequent removal) of amino protecting groups is well known within the ordinary skill of the art. Further examples of groups referred to by the above terms are described by T. W. Greene and P. G. M. Wuts, "Protective Groups in Organic Synthesis", $3^{rd}$ edition, John Wiley and Sons, New York, N.Y., 1999, chapter 7, hereafter referred to as "Greene".

The term "pharmaceutical" or "pharmaceutically acceptable" when used herein as an adjective, means substantially non-toxic and substantially non-deleterious to the recipient.

By "pharmaceutical composition" it is further meant that the carrier, solvent, excipients and/or salt must be compatible with the active ingredient of the composition (e.g. a compound of Formula I). It is understood by those of ordinary skill in this art that the terms "pharmaceutical formulation" and "pharmaceutical composition" are generally interchangeable, and they are so used for the purposes of this application.

The term "effective amount" means an amount of a compound of Formula I which is capable of antagonizing 5-HT$_7$ receptors and/or eliciting a given pharmacological effect.

The term "suitable solvent" refers to any solvent, or mixture of solvents that sufficiently solubilizes the reactants to afford a medium within which to effect the desired reaction and that does not interfere with the desired reaction.

A compound intended for use in a pharmaceutical composition may, where possible and warranted, be converted to a salt form in an effort to optimize such characteristics as the handling properties, stability, pharmacokinetics, and/or bioavailability, etc. For any compound, it is unpredictable which counterions will produce salt forms, as for example a crystalline salt form, having optimal combinations of properties for the intended use. Methods for converting a compound to a given salt form are well known in the art (see, e.g., P. Stahl, et al., Handbook of Pharmaceutical Salts: Properties, Selection and Use, (VCHA/Wiley-VCH, 2002); Berge, S. M, Bighley, L. D., and Monkhouse, D. C., *J. Pharm. Sci.*, 66:1, (1977)). Such salts are also embodiments of this invention. It is well known that salts can form in various molar ratios with the acid to provide, for example, the hemi-acid, mono-acid, di-acid salt, etc. Where in the salt formation procedure, the acid is added in a specific stoichiometric ratio, unless otherwise analyzed to confirm, the salt is presumed, but not known, to form in that molar ratio.

Abbreviations used herein are defined as follows:
"DCM" means dichloromethane.
"MS (ES)" means mass spectroscopy using electrospray ionization.
"SCX chromatography" means chromatography on a SCX column or cartridge.
"SCX column" or "SCX cartridge", as used herein, refers to a Varian Bond Elute® silica based strong cation exchange resin column or disposable cartridge or equivalent (as for example a SCX-2 cartridge).

While all of the compounds of the present invention are useful as 5-HT$_7$ antagonists, certain classes are preferred, as for example, compounds having any of the following enumerated selections of substituents:

1) $R^1$ is selected from the group consisting of methyl, ethyl, phenyl optionally substituted with 1 to 2 fluoro groups, or benzyl;
2) $R^1$ is selected from the group consisting of methyl, ethyl, and phenyl optionally substituted with 1 to 2 fluoro groups;
3) $R^1$ is methyl or ethyl;
4) $R^1$ is phenyl;
5) $R^1$ is phenyl, $R^2$ is hydrogen, $R^3$ is chloro and $R_4$ is hydroxy, hydroxymethyl or methoxymethyl;
6) $R^4$ is hydroxy, hydroxymethyl, or methoxymethyl;
7) $R^4$ is hydroxy;
8) $R^4$ is hydroxymethyl;
9) $R^4$ is methoxymethyl;
10) $R^1$ is selected from the group consisting of methyl, ethyl, and phenyl optionally substituted with 1 to 2 fluoro groups and $R^4$ is hydroxy, hydroxymethyl, or methoxymethy.

Generally, pyrazinyl compounds are preferred over pyridyl compounds. Of pyrazinyl compounds, preferred ones are those having selections of substituents according to any one of paragraphs 1 through 10 above. Likewise, of pyridyl compounds, preferred compounds are those having selections of substituents according to any one of paragraphs 1 through 10 above.

Specific preferred compounds of the present invention are those described in the Examples herein, including the free bases and the pharmaceutically acceptable salts thereof. One particularly preferred compound is 3'-[4-(1-Ethyl-5-methyl-1H-pyrazol-4-ylmethyl)-piperazin-1-yl]-3,4,5,6-tetrahydro-2H-[1,2]bipyridinyl-4-ol or a pharmaceutically acceptable salt thereof, as for example the compound of Example 1.

The compounds of the present invention can be prepared according to the following synthetic schemes by methods well known and appreciated in the art. Suitable reaction conditions for the steps of these schemes are well known in the art and appropriate substitutions of solvents and co-reagents are within the skill of the art. Likewise, it will be appreciated by those skilled in the art that synthetic intermediates may be isolated and/or purified by various well known techniques as needed or desired, and that frequently, it will be possible to use various intermediates directly in subsequent synthetic steps with little or no purification. Furthermore, the skilled artisan will appreciate that in some circumstances, the order in which moieties are introduced is not critical. The particular order of steps required to produce the compounds of Formula I is dependent upon the particular compound being synthesized, the starting compound, and the relative lability of the substituted moieties, as is well appreciated by the skilled chemist. All substituents, unless otherwise indicated, are as previously defined, and all reagents are well known and appreciated in the art.

Scheme I below shows one general synthetic route to obtain compounds of the present invention.

the free bases be converted to a salt form by means well known in the art, as for example by reaction with a pharmaceutically acceptable acid.

Alternatively, intermediates of formula VI can be reacted with piperidines VIII at elevated temperature to provide inter-

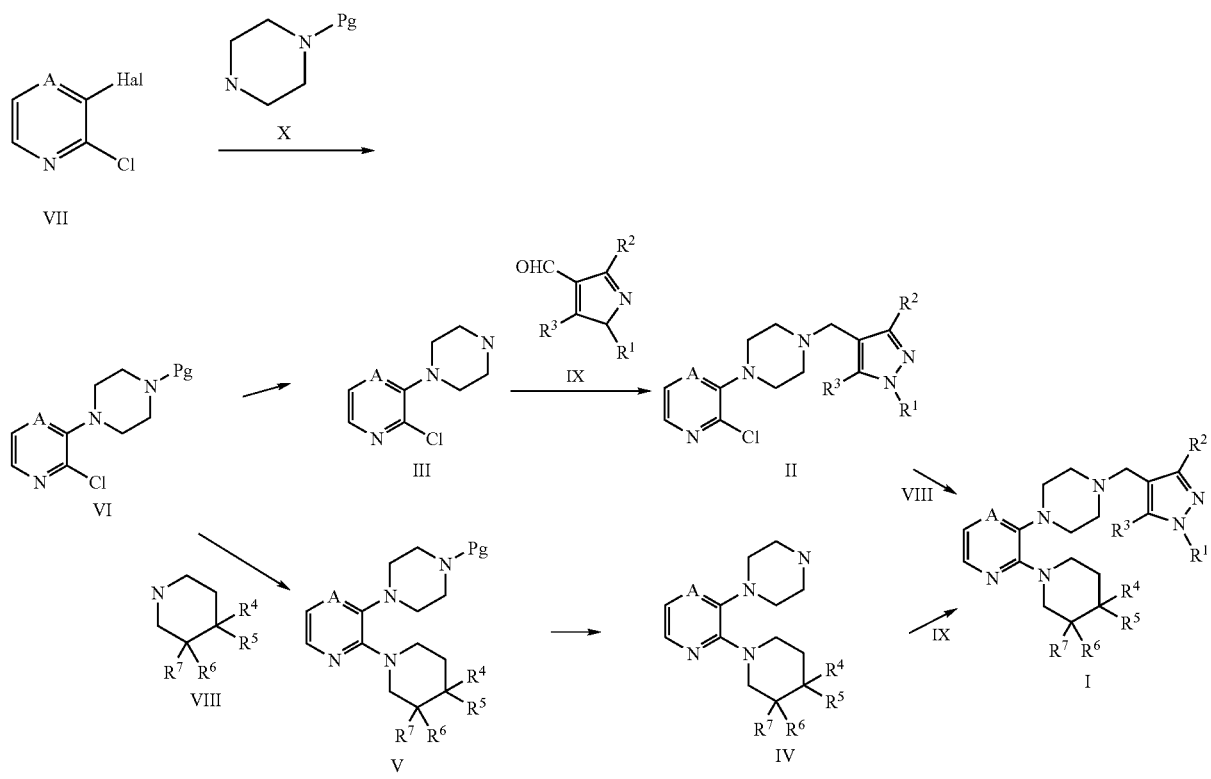

In this scheme, for compounds of formula VII wherein A is nitrogen, Hal will typically be chloro. The di-halo piperazine is reacted with N-protected piperazine and a suitable base such as potassium carbonate in an appropriate solvent such as N,N-dimethylacetamide at an elevated temperature to provide compounds of formula VI wherein A is nitrogen. For compounds of formula VII wherein A is —CH═, Hal is typically bromo or iodo. The di-halo pyridyl is coupled with N-protected piperazine under suitable catalytic coupling conditions well known in the art (John P. Wolfe and Stephen L. Buchwald. *Organic Syntheses, Coll.* Vol. 10, p. 423 (2004); Vol. 78, p. 23 (2002)) to provide compounds of formula VI (A is CH).

Compounds of formula VI can be de-protected under conditions well known to a skilled artisan (For example, see: Greene and Wuts, *Protective Groups in Organic Synthesis*, Third Edition, 1999, Chapters 2 and 7, John Wiley and Sons Inc.) to provide amines of formula III. The amines are further reacted with appropriate pyrazole aldehydes under reductive amination conditions well known to a skilled artisan (Richard C. Larock, *Comprehensive Organic Transformations*, Second Edition, 1999, Page 835-846, Wiley and Sons Inc.) to provide compounds of formula II. Compounds of formula II can then react with appropriately substituted piperidines that are either commercially available or that may be made by methods well known in the art to provide the desired free bases I. If desired, mediates of formula V. The intermediates V are then de-protected under conditions well known to the skilled artisan to provide compounds of formula IV. The resulting amines are then reacted with appropriate pyrazole aldehydes under reductive amination conditions well known to a skilled artisan to provide compounds of formula I.

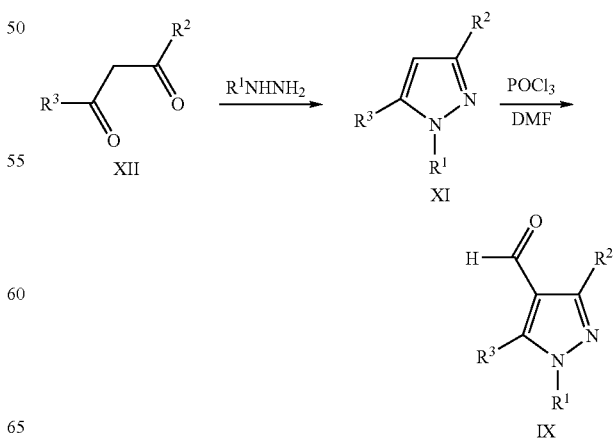

Substituted pyrazoles are either commercial available or may be synthesized by generally known procedures, as for example the procedure shown in Scheme II where variables $R^1$, $R^2$, and $R^3$ are as previously defined. When $R^2$ does not equal $R^3$, the regio-isomeric products from the cyclization must be separated with common chromatographic techniques. If XII is a labile aldehyde, XII will typically be in the form of an acetal. Compounds of formula XII are reacted with suitable hydrazines to provide compounds of formula XI. Intermediates XI are then reacted with $POCl_3$ in a suitable solvent such as dimethylformamide at an elevated temperature to provide the desired intermediates of formula IX.

Scheme III

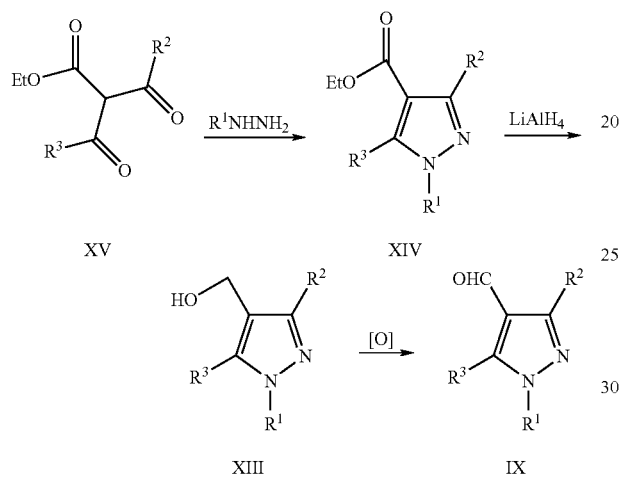

Variations on the chemistry can be used where the aldehyde precursors are incorporated into the cyclization precursors as shown in Scheme III. A compound of formula XIV reacts with a suitable hydrazine to provide a pyrazole ester of formula XIII, which is reduced with a suitable reducing agent such as $LiAlH_4$ to provide a pyrazole alcohol of formula XII. The alcohol can be oxidized with methods well known to a skilled artisan to provide the desired pyrazole aldehyde of formula IX.

The following Preparations and Examples are illustrative of methods useful for the synthesis of the compounds of the present invention. The names for many of the compounds illustrated in the preparations and examples are provided from structures drawn with ChemDraw®, version 7.0 software or Autonom 2000 for ISIS/Draw.

Preparation 1: 3'-Chloro-2,3,5,6-tetrahydro-[1,2'] bipyrazinyl-4-carboxylic acid t-butyl ester

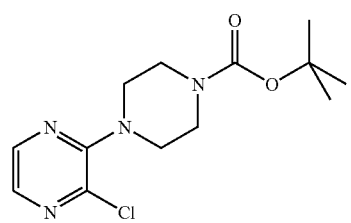

Charge a 2 L 3-neck round bottom flask with 2,3-dichloropyrazine (78.7 g, 0.532 mol), piperazine-1-carboxylic acid t-butyl ester (100 g, 0.537 mol), potassium carbonate (88.2 g, 0.638 mol) followed by N,N-dimethylacetamide (0.780 L), and heat the resultant slurry to 110° C. under nitrogen with vigorous stirring. Cool to room temperature, add water (0.390 L) and methyl t-butyl ether (0.390 L), and stir the mixture for 60 min. Stop stirring and separate the layers. Wash the organic layer with water (2×200 mL), dry over $MgSO_4$, filter and concentrate to give 145 g of 3'-chloro-2,3,5,6-tetrahydro-[1, 2']bipyrazinyl-4-carboxylic acid t-butyl ester as a yellow syrup (91% yield). $^1H$ NMR ($CDCl_3$) δ (ppm) 8.10 (s, 1H), 7.91 (s, 1H), 3.59 (m, 4H), 3.40 (m, 4H), 1.48 (s, 9H).

Preparation 2: 3'-Chloro-3,4,5,6-tetrahydro-2H-[1,2'] bipyrazinyl

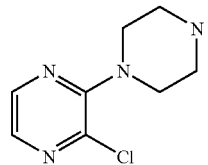

Add 4 M HCl in 1,4-dioxane (10 mL) to 3'-chloro-2,3,5,6-tetrahydro-[1,2']bipyrazinyl-4-carboxylic acid t-butyl ester (6.80 g, 22.76 mmol). Add 1,4-dioxane (40 mL) and subject the reaction to ultrasound then stir at room temperature under nitrogen for 3 hr. Add further HCl in 1,4-dioxane (40 mL) and stir for 1 hr. Add chloroform (400 mL), wash with 2 N sodium hydroxide (200 mL), saturated aqueous sodium chloride (100 mL), dry (magnesium sulfate) and concentrate to give 3'-chloro-3,4,5,6-tetrahydro-2H-[1,2']bipyrazinyl as a yellow oil which crystallized on standing to give a solid (4.0 g, 88%). MS (m/z): 199.1 (M+1).

Preparation 3: 4-(2-Chloro-pyridin-3-yl)-piperazine-1-carboxylic acid t-butyl ester

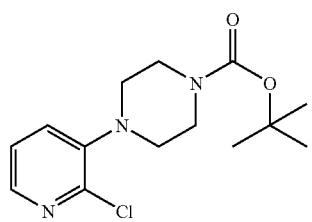

Stir 2-chloro-3-bromopyridine (5.00 g, 26.0 mmol) and piperazine-1-carboxylic acid t-butyl ester (3.73 g, 20.0 mmol) in dry toluene (200 mL) at room temperature under nitrogen. Add sodium t-butoxide (2.88 g, 30.0 mmol), tris (dibenzylideneacetone)dipalladium(0) (0.366 g, 0.40 mmol) and 4,5-bis(diphenylphosphino)-9,9-dimethylxanthene (0.694 g, 1.20 mmol), degas reaction and heat to 100° C. (oil bath temperature) for 3 hr. Cool to room temperature, add 100 mL water, extract with 2×200 mL ethyl acetate. Concentrate organic layer in vacuo, purify (silica gel chromatography, eluting with 30:70 ethyl acetate:isohexane) and dry in a vacuum oven over night to give 4-(2-chloro-pyridin-3-yl)- piperazine-1-carboxylic acid t-butyl ester as a beige powder (3.01 g, 51%). MS (m/z): 298 (M+1).

Preparation 4: 1-(2-Chloro-pyridin-3-yl)-piperazine

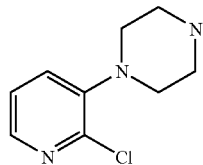

Stir 4-(2-chloro-pyridin-3-yl)-piperazine-1-carboxylic acid t-butyl ester (2.00 g, 6.72 mmol) in DCM (50 mL) at room temperature, then add trifluoroacetic acid (5 mL). Stir the reaction for 2 hr. and remove solvents in vacuo, then form the free base using SCX-2® chromatography washing with methanol then eluting with around 3 M ammonia in methanol. Concentrate in vacuo to give 1-(2-chloro-pyridin-3-yl)-piperazine as a brown oil (1.47 g, 110% yield). MS (m/z): 198 (M+1).

Preparation 5: 1-(3-Fluoro-phenyl)-3-methyl-1H-pyrazole

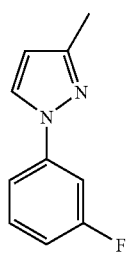

Add hydrochloric acid (5M, 12 mL, 60 mmol) to a mixture of 4,4-dimethoxybuta-2-one (6.61 g, 6.67 mL, 50 mmol) and 3-fluorophenylhydrazine hydrochloride (8.13 g, 50 mmol) in ethanol (50 mL). Heat and stir under reflux under nitrogen for 7.5 hr., cool to room temperature, allow to stand for 60 hr. Evaporate the ethanol in vacuo, and chromatograph the residue on silica eluting with DCM. Evaporate the dichloromethane to give 1-(3-fluoro-phenyl)-3-methyl-1H-pyrazole as a liquid (4.38 g, 49%). MS (m/z): 171.1 (M+1).

Preparation 6: 1-(2,5-Difluoro-phenyl)-1H-pyrazole

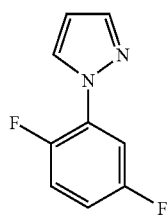

Add 1,1,3,3-tetramethoxypropane (8.2 g, 50 mmol) to a mixture of 2,5-difluorophenylhydrazine (9.022 g, 62.6 mmol) and hydrochloric acid (5M, 5 mL, 25 mmol) in ethanol (50 mL) and heat and stir under reflux under nitrogen for 17 hr. Cool the mixture, evaporate the ethanol in vacuo, suspend the residue in DCM (80 mL), filter the DCM solution and pass through an SCX-2 column. Collect the eluent and pass through a second SCX2 column and evaporate the eluent to give 1-(2,5-difluoro-phenyl)-1H-pyrazol as a liquid (8.79 g, 97%). MS (m/z): 181 (M+1).

Preparation 7: 1-(3-Fluoro-phenyl)-3-methyl-1H-pyrazole-4-carbaldehyde

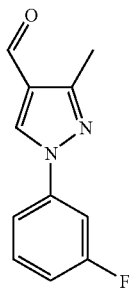

Add phosphorus oxychloride (20.8 mL, 34.3 g, 223.7 mmol) dropwise with stirring at 95° C. under nitrogen to 1-(3-fluoro-phenyl)-3-methyl-1H-pyrazole (4.38 g, 24.86 mmol) in dimethylformamide (19.2 mL, 18.17 g, 248.6 mmol). Heat at 95° C. for 15 hr., cool to room temperature, pour over ice and neutralize with sodium hydrogen carbonate. Extract the aqueous solution with ethyl acetate (2×150 mL), dry (magnesium sulfate), filter, and pass through an SCX-2 column. Evaporate the solvent to give 1-(3-fluoro-phenyl)-3-methyl-1H-pyrazole-4-carbaldehyde as a solid. (4.22 g, 83%). MS (m/z): 205.1 (M+1).

Preparation 8: 1-(2,5-Difluoro-phenyl)-1H-pyrazole-4-carbaldehyde

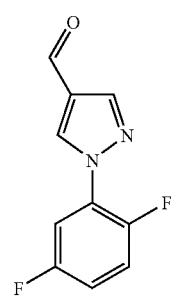

The title intermediate is prepared using methods similar to those of Preparation 7 using 1-(2,5-di-fluoro-phenyl)-1H-pyrazole. MS (ES) [M+H] 209.1.

Preparation 9:
5-Methyl-1-pyridin-2-yl-1H-pyrazole-4-carbaldehyde

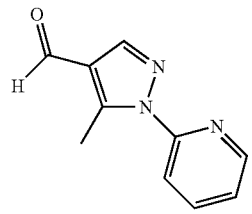

2-Dimethylaminomethylene-3-oxo-butyric acid ethyl ester

Add ethyl acetoacetate (15 mL, 0.118 mol) to dimethoxymethyl-dimethyl-amine (19 mL, 0.142 mol) and reflux the mixture for 1 hr. Evaporate the mixture to give 2-dimethylaminomethylene-3-oxo-butyric acid ethyl ester (21.7 g, 99%).

5-Methyl-1-pyridin-2-yl-1H-pyrazole-4-carboxylic acid ethyl ester

Dissolve 2-dimethylaminomethylene-3-oxo-butyric acid ethyl ester (0.662 g, 3.57 mmol) and pyridin-2-yl-hydrazine (0.410 g, 3.75 mmol) in ethanol (15 mL) and reflux for 2 hr. Evaporate the mixture then dilute with saturated sodium bicarbonate and extract three times with ethyl acetate. Dry the solution (sodium sulfate), filter and concentrate. Purify using silica gel chromatography, eluting with 50:50 ethyl acetate:hexane to give 5-methyl-1-pyridin-2-yl-1H-pyrazole-4-carboxylic acid ethyl ester as a white solid (0.700 g, 85%). MS (m/z): 232 (M+1).

(5-Methyl-1-pyridin-2-yl-1H-pyrazol-4-yl)-methanol

Add lithium aluminum hydride (0.225 g, 5.92 mmol) to tetrahydrofuran (15 mL) at 0° C. then slowly add 5-methyl-1-pyridin-2-yl-1H-pyrazole-4-carboxylic acid ethyl ester (0.685 g, 2.96 mmol) in tetrahydrofuran (5 mL) dropwise. Warm the mixture to room temperature and stir for two hr. then cool the solution to 0° C. Add saturated aqueous sodium sulfate (0.5 mL), warm to room temperature then stir for 2 hr. Filter off the solid materials then dry the solution (sodium sulfate), filter and concentrate to give (5-methyl-1-pyridin-2-yl-1H-pyrazol-4-yl)-methanol as a white solid (0.501 g, 89%).

5-Methyl-1-pyridin-2-yl-1H-pyrazole-4-carbaldehyde

Dissolve dimethyl sulfoxide (0.751 mL, 10.6 mmol) in DCM (20 mL) and cool to −78° C. Add oxalyl chloride (0.577 mL, 6.62 mmol) dropwise in DCM (8 mL) and stir for 15 min. Add (5-methyl-1-pyridin-2-yl-1H-pyrazol-4-yl)-methanol (0.501 g, 2.65 mmol) in DCM (20 mL) dropwise and stir for 1 hr. at −78° C. Add triethylamine (1.85 mL, 13.2 mmol) and warm the mixture to room temperature for 1 hr. Dilute the mixture with saturated sodium bicarbonate and extract three times with DCM. Dry (sodium sulfate) the solution, filter and concentrate to give 5-methyl-1-pyridin-2-yl-1H-pyrazole-4-carbaldehyde as a white solid (0.496 g, 100%). MS (m/z): 188 (M+1).

Preparation 10:
3-Ethyl-1-phenyl-1H-pyrazole-4-carbaldehyde

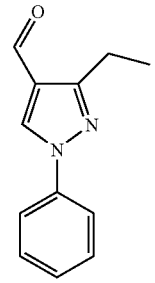

N-[1-Methyl-prop-(E)-ylidene]-N'-phenyl-hydrazine

Add acetic acid (1.00 mL, 17.45 mmol) and phenyl hydrazine (1.98 mL, 20.00 mmol) to a solution of 2-butanone (2.15 mL, 24.00 mmol) in ethanol (90 mL) at room temperature. Stir the reaction for 1 hr., then remove the solvents in vacuo to give a N-[1-methyl-prop-(E)-ylidene]-N'-phenyl-hydrazine as a crude orange oil (3.21 g, 99%). MS (m/z): 163 (M+1).

3-Ethyl-1-phenyl-1H-pyrazole-4-carbaldehyde

To an ice cold solution of N,N-dimethylformamide (4.59 mL, 59.36 mmol) and phosphoryl chloride (5.52 mL, 59.36 mmol) add a solution of N-[1-methyl-prop-(E)-ylidene]-N'-phenyl-hydrazine (3.21 g, 19.79 mmol) in N,N-dimethylformamide (2 mL) dropwise. Warm to room temperature, then heat to 75° C. for 5 hr. Cool to room temperature and pour into an ice-cold solution of saturated potassium carbonate. Extract with DCM (3×20 mL), pass through an IST Phase Separator Frit® and concentrate. Purify (silica gel chromatography, eluting with 0:100 to 20:80 ethyl acetate:isohexane), to give 3-ethyl-1-phenyl-1H-pyrazole-4-carbaldehyde as brown solid (600 mg, 15%). MS (m/z): 201 (M+1).

Preparation 11: 3,5-Dimethyl-1-pyridin-2-yl-1H-pyrazole-4-carbaldehyde

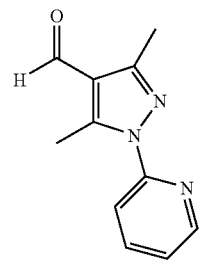

3,5-Dimethyl-1-pyridin-2-yl-1H-pyrazole-4-carboxylic acid ethyl ester

Dissolve 2-acetyl-3-oxobutyric acid ethyl ester (20.74 g, 0.120 mol) and 2-pyridylhydrazine (14.5 mL, 0.133 mol) in acetic acid (160 mL) and stir the mixture for 18 hr. Concentrate, dilute with DCM, wash with saturated sodium bicarbonate, dry (sodium sulfate), filter and concentrate to give 3,5-dimethyl-1-pyridin-2-yl-1H-pyrazole-4-carboxylic acid ethyl ester as an oil (28.6 g, 97%). MS (m/z): 246 (M+1).

(3,5-Dimethyl-1-pyridin-2-yl-1H-pyrazol-4-yl)-methanol

Suspend lithium aluminum hydride (0.359 g, 9.46 mmol) in tetrahydrofuran (25 mL) at −10° C. and add 3,5-dimethyl-1-pyridin-2-yl-1H-pyrazole-4-carboxylic acid ethyl ester (1.160 g, 4.73 mmol) dropwise in tetrahydrofuran (5 mL). Allow the mixture to warm to 25° C. and stir for 4 hr. Cool the mixture to 0° C. then quench carefully with saturated sodium sulfate solution (1 mL). Allow the mixture to stir at room temperature for 2 hr. then filter off the precipitate, dry the solution and concentrate to give (3,5-dimethyl-1-pyridin-2-yl-1H-pyrazol-4-yl)-methanol as a yellow solid (0.821 g, 86%).

3,5-Dimethyl-1-pyridin-2-yl-1H-pyrazole-4-carbaldehyde

Dissolve dimethylsulfoxide (0.324 mL, 4.56 mmol) in DCM (10 mL) and cool the solution to −78° C. Add oxalyl chloride (0.239 mL, 2.74 mmol) to the mixture dropwise and stir at −78° C. for 20 min. Add (3,5-dimethyl-1-pyridin-2-yl-1H-pyrazol-4-yl)-methanol (0.369 g, 1.82 mmol) in DCM (10 mL) and stir the mixture at −78° C. for 1 hr. Add triethylamine (1.27 mL, 9.12 mmol) to the mixture and warm to room temperature then stir for 18 hr. Add saturated aqueous sodium bicarbonate and extract the aqueous 3 times with DCM, dry organic solution then filter and concentrate. Purify using silica gel chromatography, eluting with 20:80 hexanes: ethyl acetate to give 3,5-dimethyl-1-pyridin-2-yl-1H-pyrazole-4-carbaldehyde as a yellow solid (0.358 g, 97%). MS (m/z): 202 (M+1).

Preparation 12:
1-(2-Hydroxy-ethyl)-1H-pyrazole-4-carbaldehyde

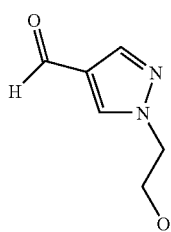

Combine 1H-pyrazole-4-carbaldehyde (0.110 g, 1.14 mmol), 2-bromoethanol (0.172 g, 1.37 mmol), and potassium carbonate (0.236 g, 1.71 mmol) in acetonitrile (2 mL). Heat in microwave at 150° C. for 20 min. Cool to room temperature and filter, wash with acetonitrile. Concentrate filtrate to give 1-(2-hydroxy-ethyl)-1H-pyrazole-4-carbaldehyde (0.155 g, 97%). GC-MS (m/z): 140 (M+).

Preparation 13:
N-Piperidin-4-ylmethyl-methanesulfonamide

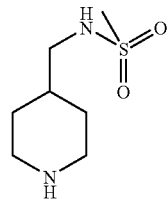

To a solution of t-butyl 4-(aminomethyl)tetrahydropyridine-1(2H)-carboxylate (1.50 g, 7.0 mmol, 1 eq) in DCM (anhydrous) (20 mL) is added methanesulfonyl chloride (569 µL, 7.35 mmol, 1.05 eq). To this add triethylamine (2.05 ml, 14.7 mmol, 2.1 eq), dropwise over 15 min. Stir at room temperature for 3 hr. and then add water (20 mL) with stirring. The organic phase is isolated then washed with 2 M aqueous hydrochloric acid (20 mL), and saturated aqueous sodium hydrogen carbonate solution (20 mL). Dry the organic layer (magnesium sulphate) and concentrate to give 4-(methanesulfonyl-aminomethyl)-piperidine-1-carboxylic acid t-butyl ester (2.1 g, 102%). MS (ES): m/z=315.1 [M+Na]⁺. To a solution of this compound (2.1 g, 7.2 mmol, 1 eq) in 1,4-dioxane (25 mL) add 4 M hydrogen chloride in dioxane (17.95 mL, 72 mmol, 10 eq). Stir at room temperature for 29 hr., basify with 2 M aqueous sodium hydroxide, and then add DCM (20 mL). Separate the layers and extract the aqueous twice with DCM (20 mL), dry the combined organics over magnesium sulphate, filter and concentrate. Extract the aqueous layer a further four times with 3:1 chloroform:isopropanol (25 mL). Concentrate the aqueous layer to less than 10 mL volume and extract again with four times with 3:1 chloroform:isopropanol (25 mL). Combine with all the previous organic extracts to give N-piperidin-4-ylmethyl-methanesulfonamide (703 mg, 50%). MS (m/z): 193 (M+1).

Preparation 14: Piperidin-4-yl-acetonitrile

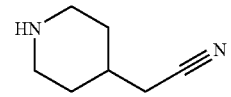

4-Cyanomethylenepiperidine-1-carboxylic acid t-butyl ester

Add diethyl cyanomethylphosphonate (5.33 g, 4.88 mL, 30.11 mmol) to potassium carbonate (3.47 g, 25.09 mmol) in dry THF (10 mL) and stir at room temperature for 15 min., then heat under reflux for 15 min. To this mixture add 4-oxopiperidine-1-carboxylic acid t-butyl ester (5.00, 25.09 mmol) and heat under reflux under nitrogen for 24 hr., allow to cool to room temperature and stand overnight. Pour the reaction mixture into aqueous potassium carbonate solution (10%, 80 mL) and extract the resultant mixture with ethyl acetate (2×50 mL). Combine the organics, dry (MgSO₄) and evaporate in vacuo to give 4-cyanomethylenepiperidine-1- carboxylic acid t-butyl ester as a liquid which solidifies on standing (5.39 g, 96.6%). NMR (δ-CDCl₃) 1.5 (s, 9H), 2.4 (m, 2H), 2.6 (m, 2H), 3.5 (m, 4H), 5.2 (s, 1H).

4-Cyanomethylpiperidine-1-carboxylic acid t-butyl ester

Add 4-cyanomethylenepiperidine-1-carboxylic acid t-butyl ester (5.39 g, 24.25 mmol) in ethanol (160 mL) to a suspension of 5% palladium on charcoal (0.69 g) in ethanol (20 mL) and hydrogenate at room temperature with agitation at 60 psi for 6 hr. Filter the mixture through celite and evaporate the solvent in vacuo to give 4-cyanomethylpiperidine-1-carboxylic acid t-butyl ester as an oil which solidifies on standing to give a solid (5.43 g, 99.8%). MS (m/z): 247 (M+Na).

Piperidin-4-ylacetonitrile

Add trifluoroacetic acid (23 mL, 34.7 g, 304 mmol) to 4-cyanomethylpiperidine-1-carboxylic acid t-butyl ester (5.43 g, 24.21 mmol) in DCM (25 mL) and stir at room temperature for 18 hr. Remove the solvent in vacuo and dissolve in methanol (50 mL) and pour onto an SCX-2 column. Elute with 2 M ammonia in methanol and evaporate the eluent to give piperidin-4-ylacetonitrile as an oil which solidifies on standing (2.78 g, 92%). MS (m/z): 125.1 (M+1).

Preparation 15: 3'-Chloro-4-(1,5-dimethyl-1H-pyrazol-4-ylmethyl)-3,4,5,6-tetrahydro-2H-[1,2']bipyrazinyl

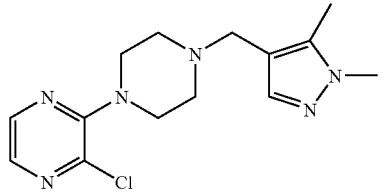

Charge a 2 L 3-neck round bottom flask with 3'-chloro-3,4,5,6-tetrahydro-2H-[1,2']bipyrazinyl (39 g, 0.196 mol), 1,2-dichloroethane (780 mL), followed by 1,5-dimethyl-1H-pyrazole-4-carbalehyde (25.5 g, 0.206 mol) and stir for 15 min. under nitrogen with vigorous stirring. Add sodium triacetoxyborohydride (45.77 g, 215 mmol) in three portions, 10 min. apart. Add methanol (100 mL) slowly and stir for 20 min. and concentrate to a white foam. Dissolve the foam in methylene chloride and add to a 1 kg silica plug. Elute the product with 5-10% isopropyl alcohol/DCM and concentrate the product containing fractions to give 3'-chloro-4-(1,5-dimethyl-1H-pyrazol-4-ylmethyl)-3,4,5,6-tetrahydro-2H-[1,2']bipyrazinyl as a yellow oil (37 g, 60%). MS (m/z): 307 (M+1).

The following compounds are prepared essentially by the methods of Preparation 15 using the appropriate 2-chloro-3-(piperazin-1-yl)pyrazine or 1-(2-chloro-pyridin-3-yl)piperazine, and substituted-1H-pyrazole-4-carbaldehyde.

| Prep | Compound | Structure | MS (ES) [M + H] |
|---|---|---|---|
| 16 | 4-(1-Benzyl-1H-pyrazol-4-ylmethyl)-3'-chloro-3,4,5,6-tetrahydro-2H-[1,2']bipyrazinyl | 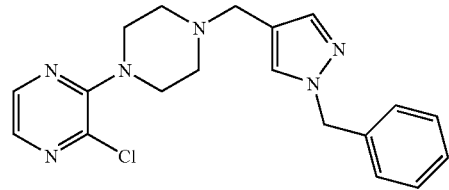 | 369.1 |
| 17 | 4-(1-Benzyl-3,5-dimethyl-1H-pyrazol-4-ylmethyl)-3'-chloro-3,4,5,6-tetrahydro-2H-[1,2']bipyrazinyl | 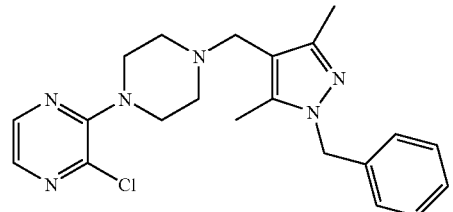 | 397.1 |
| 18 | 3'-Chloro-4-[1-(3-fluorophenyl)-1H-pyrazol-4-ylmethyl]-3,4,5,6-tetrahydro-2H-[1,2']bipyrazinyl | 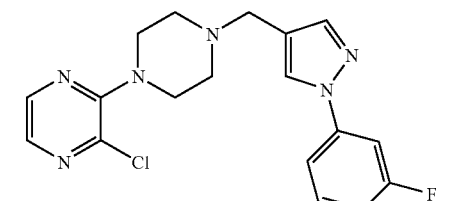 | 373.1 |

-continued

| Prep | Compound | Structure | MS (ES) [M + H] |
|---|---|---|---|
| 19 | 3'-Chloro-4-[1-(3-fluoro-phenyl)-3-methyl-1H-pyrazol-4-ylmethyl]-3,4,5,6-tetrahydro-2H-[1,2']bipyrazinyl | 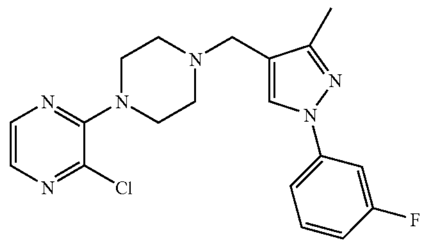 | 387.1 |
| 20 | 3'-Chloro-4-[1-(2-fluoro-phenyl)-1H-pyrazol-4-ylmethyl]-3,4,5,6-tetrahydro-2H-[1,2']bipyrazinyl | 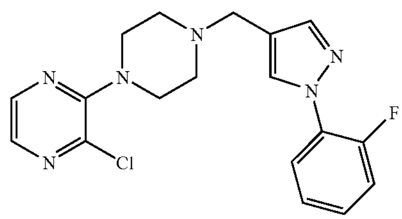 | 372.9 |
| 21 | 3'-Chloro-4-[1-(2,5-difluoro-phenyl)-1H-pyrazol-4-ylmethyl]-3,4,5,6-tetrahydro-2H-[1,2']bipyrazinyl | 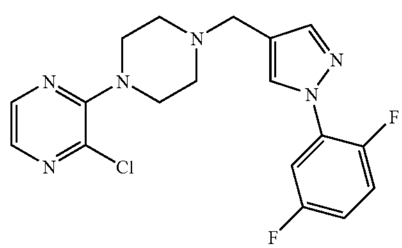 | 391.1 |
| 22 | 2-[4-(3'-Chloro-2,3,5,6-tetrahydro-[1,2']bipyrazinyl-4-ylmethyl)-pyrazol-1-yl]-ethanol | 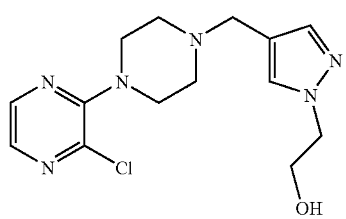 | 323.1 |
| 23 | 3'-Chloro-4-(3-methyl-1-phenyl-1H-pyrazol-4-ylmethyl)-3,4,5,6-tetrahydro-2H-[1,2']bipyrazinyl | 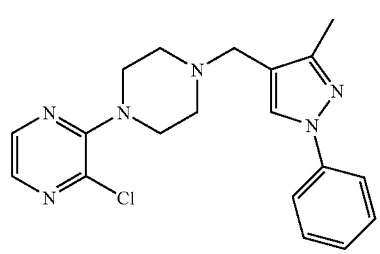 | 369 |
| 24 | 1-(2-Chloro-pyridin-3-yl)-4-(1,5-dimethyl-1H-pyrazol-4-ylmethyl)-piperazine | 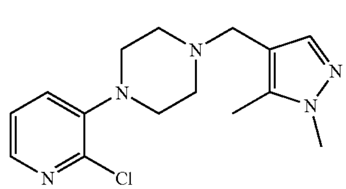 | 306 |
| 25 | 1-(2-Chloro-pyridin-3-yl)-4-(1-ethyl-5-methyl-1H-pyrazol-4-ylmethyl)-piperazine | 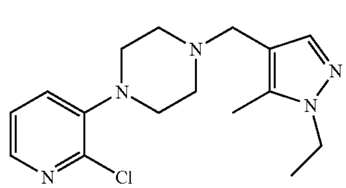 | 320.1 |

| Prep | Compound | Structure | MS (ES) [M + H] |
|------|----------|-----------|-----------------|
| 26 | 1-(2-Chloro-pyridin-3-yl)-4-(5-methyl-1-phenyl-1H-pyrazol-4-ylmethyl)-piperazine | 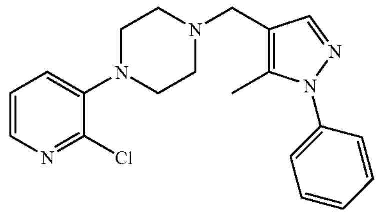 | 368 |
| 27 | 1-(2-Chloro-pyridin-3-yl)-4-(3-methyl-1-phenyl-1H-pyrazol-4-ylmethyl)-piperazine | 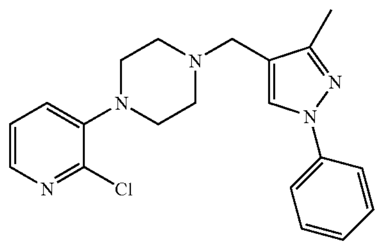 | 368 |

Preparation 28: 3'-Piperidin-1-yl-3,4,5,6-tetrahydro-2H-[1,2']bipyrazinyl

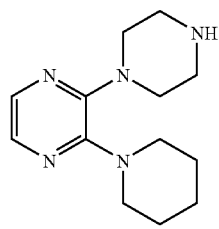

3'-Piperidin-1-yl-2,3,5,6-tetrahydro-[1,2']bipyrazinyl-4-carboxylic acid t-butyl ester Place 3'-chloro-2,3,5,6-tetrahydro-[1,2']bipyrazinyl-4-carboxylic acid t-butyl ester (0.4 g, 1.34 mmol, 1 eq) and piperidine (662 μL, 6.69 mmol, 5 eq) in a microwave vial, seal and heat in a CEM™ microwave to 180° C. with up to 300 Watt power for 1 hr. (Caution—pressure build up). Add 2 M aqueous sodium hydroxide solution (5 mL) and DCM (5 mL), and then pass through a hydrophobic frit to separate. Extract the aqueous layer twice with DCM (5 mL) combine the organic extracts and concentrate to give 3'-piperidin-1-yl-2,3,5,6-tetrahydro-[1,2']bipyrazinyl-4-carboxylic acid t-butyl ester (0.46 g, 99%). MS (m/z): 348.3 (M+1).

3'-Piperidin-1-yl-3,4,5,6-tetrahydro-2H-[1,2']bipyrazinyl

Add trifluoroacetic acid (1.00 mL, 13.24 mmol, 10 eq) to a solution of 3'-piperidin-1-yl-2,3,5,6-tetrahydro-[1,2']bipyrazinyl-4-carboxylic acid t-butyl ester (0.46 g, 1.32 mmol, 1 eq) in DCM (10 mL) then stir the mixture at room temperature for 4 hr. Concentrate the reaction mixture, then dissolve in methanol and load on to a 10 g SCX-2 ion exchange cartridge (pre-washed with methanol). Wash with one column volume of methanol then elute with one column volume of 3.5 M ammonia in methanol. Concentrate to give 3'-piperidin-1-yl-3,4,5,6-tetrahydro-2H-[1,2']bipyrazinyl (0.317 g, 0.97%). MS (m/z): 248.2 (M+1).

The following compounds are prepared essentially by the method of Preparation 28 using tert-butyl 4-(2-chloropyridin-3-yl)piperizine-1-carboxylate or tert-butyl 4-(3-chloropyrazin-2-yl)piperizine-1-carboxylate and substituted piperidine.

| Preparation | Compound | Structure | MS (ES) [M + H] |
|-------------|----------|-----------|-----------------|
| 29 | 1-(3,4,5,6-Tetrahydro-2H-[1,2']bipyrazinyl-3'-yl)-piperidin-4-ol | 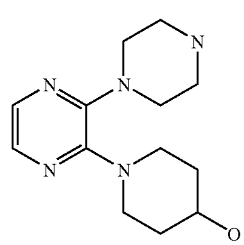 | 264.3 |

-continued

| Preparation | Compound | Structure | MS (ES) [M + H] |
|---|---|---|---|
| 30 | 3'-(4-Methyl-piperidin-1-yl)-3,4,5,6-tetrahydro-2H-[1,2']bipyrazinyl | 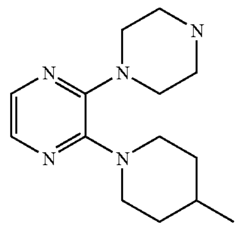 | 262.2 |
| 31 * | [1-(3,4,5,6-Tetrahydro-2H-[1,2']bipyrazinyl-3'-yl)-piperidin-4-yl]-methanol | 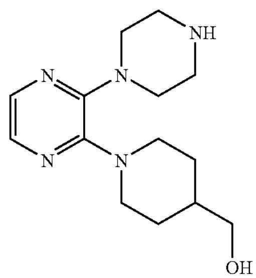 | 278 |
| 32 | 3'-(4-Fluoro-piperidin-1-yl)-3,4,5,6-tetrahydro-2H-[1,2']bipyrazinyl | 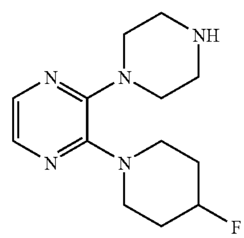 | 266 |
| 33 * | (3'-Piperazin-1-yl-3,4,5,6-tetrahydro-2H-[1,2']bipyridinyl-4-yl)-methanol | 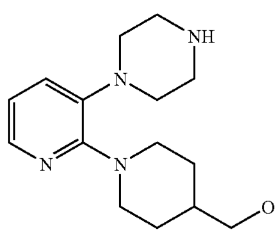 | 277.1 |

* These intermediates do not require the deprotection step of preparation 27 in that N-protecting Boc group is removed under the microwave conditions.

Preparation 34: Toluene-4-sulfonic acid 1-[4-(1,5-dimethyl-1H-pyrazol-4-ylmethyl)-3,4,5,6-tetrahydro-2H-[1,2']bipyrazinyl-3'-yl]-piperidin-4-ylmethyl ester

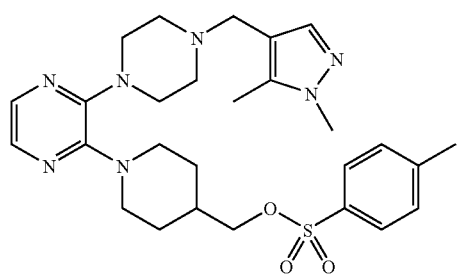

Add p-toluenesulfonyl chloride (272 mg, 1.43 mmol, 1.1 eq) to a solution of {1-[4-(1,5-dimethyl-1H-pyrazol-4-ylmethyl)-3,4,5,6-tetrahydro-2H-[1,2']bipyrazinyl-3'-yl]-piperidin-4-yl}-methanol (0.5 g, 1.30 mmol, 1 eq, free base and triethylamine (1.43 mL, 10.24 mmol, 1.1 eq) in DCM (3 mL) at 0° C. Stir the mixture under nitrogen for 20.5 hr. Add a further portion of p-toluenesulfonyl chloride (0.13 g, 0.682 mmol, 0.5 eq) to the reaction mixture and continue stirring for a further 4.5 hr. Quench the reaction with saturated aqueous sodium bicarbonate solution (20 mL), and then pass through a hydrophobic frit to separate. Wash the aqueous layer twice with DCM (20 mL), combine the organic extracts and concentrate. Purify by flash chromatography on 40 g silica gel column, eluting with 0-10% methanol in DCM to give toluene-4-sulfonic acid 1-[4-(1,5-dimethyl-1H-pyrazol-4-ylmethyl)-3,4,5,6-tetrahydro-2H-[1,2']bipyrazinyl-3'-yl]-piperidin-4-ylmethyl ester (0.36 g, 51%). MS (m/z): 540.2 (M+1).

EXAMPLE 1

3'-[4-(1-Ethyl-5-methyl-1H-pyrazol-4-ylmethyl)-piperazin-1-yl]-3,4,5,6-tetrahydro-2H-[1,2]bipyridinyl-4-ol hydrochloride

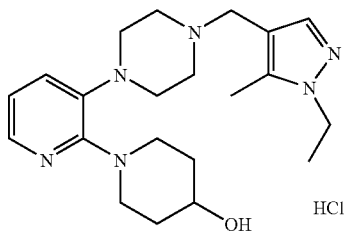

Place 1-(2-chloro-pyridin-3-yl)-4-(1-ethyl-5-methyl-1H-pyrazol-4-ylmethyl)-piperazine (0.155 mg, 0.484 mmol, 1 eq) and 4-hydroxypiperidine (245.09 mg, 2.42 mmol, 5 eq) in a microwave vial, seal and heat in a CEM™ microwave to 180° C. with up to 300 Watt power for 1 hr. Put the cooled mixture back on to react for a further 1 hr. under the same conditions. Add water (5 mL) and DCM (5 mL) to the cooled reaction mixture and then pass through a hydrophobic frit to separate. Extract the aqueous layer twice with DCM (5 mL) combine the organic extracts and concentrate. Purify by flash chromatography on a 40 g silica gel column, eluting with 4-8% methanol in DCM. Dissolve this material (101 mg, 0.26 mmol) in the minimum quantity of 50% aqueous acetonitrile. Add 2M aqueous hydrogen chloride (130 µL, 0.26 mmol) and lyophilize to give 3'-[4-(1-ethyl-5-methyl-1H-pyrazol-4-ylmethyl)-ppiperazin-1-yl]-3,4,5,6-tetrahydro-2H-[1,2]bipyridinyl-4-ol hydrochloride (111 mg, 54%). MS (m/z): 385.2 (M+1).

The following compounds are prepared essentially by the method of Example 1 using the appropriate 4-(substituted-1H-pyrazol-4-ylmethyl)-1-(2-chloro-pyridin-3-yl)piperazine or 4-(substituted-1H-pyrazol-4-ylmethyl)-1-(2-chloro-pyrazin-3-yl)piperazine, and substituted piperidine.

| Example | Compound | Structure | MS (ES) [M + H] |
|---|---|---|---|
| 2 | {3'-[4-(1,5-Dimethyl-1H-pyrazol-4-ylmethyl)-piperazin-1-yl]-3,4,5,6-tetrahydro-2H-[1,2']bipyridinyl-4-yl}-methanol hydrochloride | 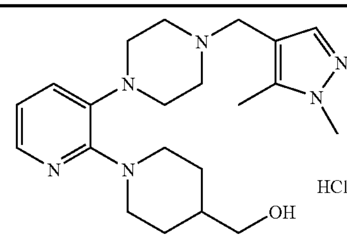 | 385.2 |
| 3 | {3'-[4-(5-Methyl-1-phenyl-1H-pyrazol-4-ylmethyl)-piperazin-1-yl]-3,4,5,6-tetrahydro-2H-[1,2']bipyridinyl-4-yl}-methanol hydrochloride | 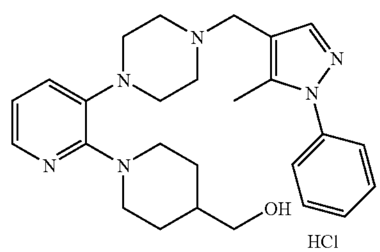 | 447.2 |
| 4 | {3'-[4-(1-Ethyl-5-methyl-1H-pyrazol-4-ylmethyl)-piperazin-1-yl]-3,4,5,6-tetrahydro-2H-[1,2']bipyridinyl-4-yl}-methanol hydrochloride | 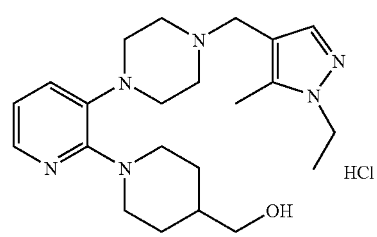 | 399.2 |
| 5 | {3'-[4-(3-Methyl-1-phenyl-1H-pyrazol-4-ylmethyl)-piperazin-1-yl]-3,4,5,6-tetrahydro-2H-[1,2']bipyridinyl-4-yl}-methanol hydrochloride | 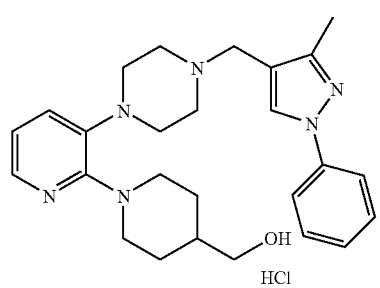 | 447.2 |

-continued

| Example | Compound | Structure | MS (ES) [M + H] |
|---|---|---|---|
| 6 | 4-(1,5-Dimethyl-1H-pyrazol-4-ylmethyl)-3'-piperidin-1-yl-3,4,5,6-tetrahydro-2H-[1,2']bipyrazinyl hydrochloride | 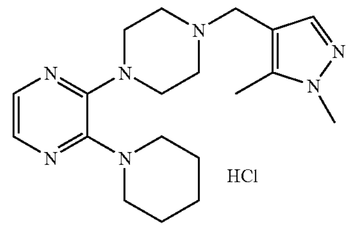 | 356.2 |
| 7 | 4-(1,5-Dimethyl-1H-pyrazol-4-ylmethyl)-3'-(4-methyl-piperidin-1-yl)-3,4,5,6-tetrahydro-2H-[1,2']bipyrazinyl hydrochloride | 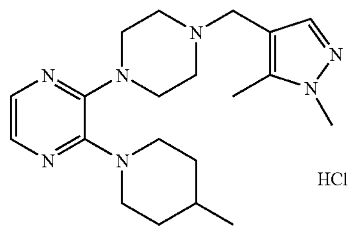 | 370.2 |
| 8 | 3'-(3,3-Dimethyl-piperidin-1-yl)-4-(1,5-dimethyl-1H-pyrazol-4-ylmethyl)-3,4,5,6-tetrahydro-2H-[1,2']bipyrazinyl hydrochloride | 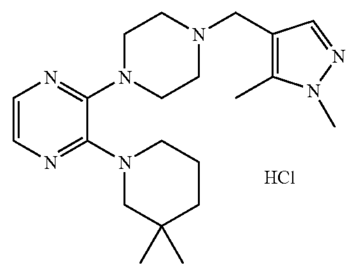 | 384.3 |
| 9 | 4-(1,5-Dimethyl-1H-pyrazol-4-ylmethyl)-3'-(4-methoxymethyl-piperidin-1-yl)-3,4,5,6-tetrahydro-2H-[1,2']bipyrazinyl hydrochloride | 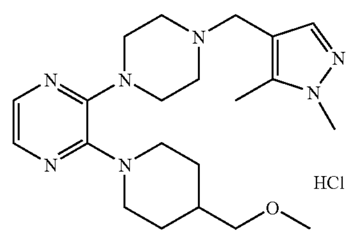 | 400.2 |
| 10 | 2-{1-[4-(1,5-Dimethyl-1H-pyrazol-4-ylmethyl)-3,4,5,6-tetrahydro-2H-[1,2']bipyrazinyl-3'-yl]-piperidin-4-yl}-ethanol hydrochloride | 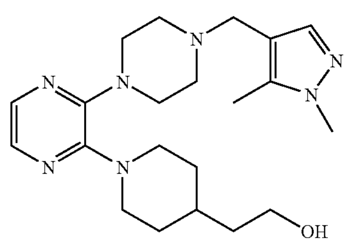 | 400.2 |
| 11 | 1-[4-(1,5-Dimethyl-1H-pyrazol-4-ylmethyl)-3,4,5,6-tetrahydro-2H-[1,2']bipyrazinyl-3'-yl]-piperidin-4-ol hydrochloride | 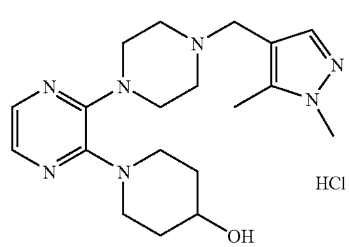 | 372.2 |

-continued

| Example | Compound | Structure | MS (ES) [M + H] |
|---|---|---|---|
| 12 | {1-[4-(1,5-Dimethyl-1H-pyrazol-4-ylmethyl)-3,4,5,6-tetrahydro-2H-[1,2']bipyraziny[3'-yl]-piperidin-4-yl}-methanol hydrochloride | 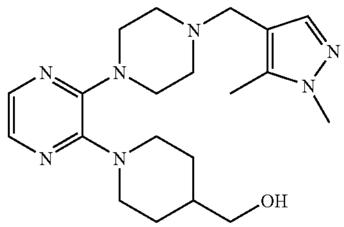 | 386.2 |
| 13 *** | N-{1-[4-(1,5-Dimethyl-1H-pyrazol-4-ylmethyl)-3,4,5,6-tetrahydro-2H-[1,2']bipyrazinyl-3'-yl]-piperidin-4-ylmethyl}-methanesulfonamide hydrochloride | 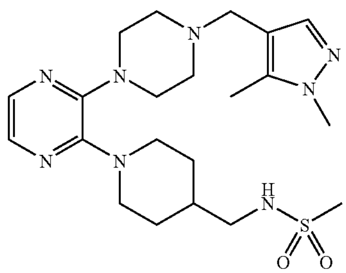 | 463.2 |
| 14 | 1-[4-(1-Benzyl-3,5-dimethyl-1H-pyrazol-4-ylmethyl)-3,4,5,6-tetrahydro-2H-[1,2']bipyrazinyl-3'-yl]-piperidin-4-ol hydrochloride | 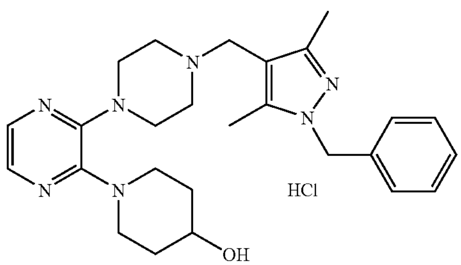 | 462.2 |
| 15 * *** | 4-(1,5-Dimethyl-1H-pyrazol-4-ylmethyl)-3'-(4-fluoro-piperidin-1-yl)-3,4,5,6-tetrahydro-2H-[1,2']bipyrazinyl hydrochloride | 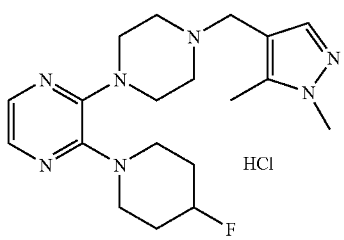 | 374.2 |
| 16 ** | 3'-(4,4-Difluoro-piperidin-1-yl)-4-(1,5-dimethyl-1H-pyrazol-4-ylmethyl)-3,4,5,6-tetrahydro-2H-[1,2']bipyrazinyl hydrochloride | 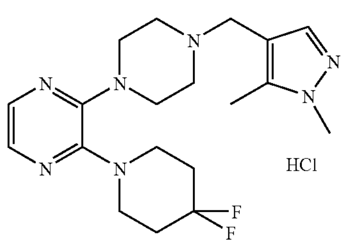 | 392.1 |
| 17 ** | 3'-(3,3-Difluoro-piperidin-1-yl)-4-(1,5-dimethyl-1H-pyrazol-4-ylmethyl)-3,4,5,6-tetrahydro-2H-[1,2']bipyrazinyl hydrochloride | 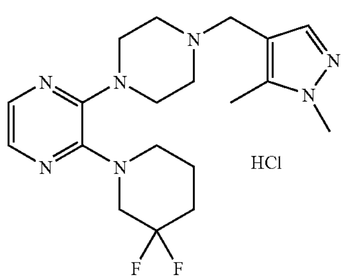 | 392.1 |

-continued

| Example | Compound | Structure | MS (ES) [M + H] |
|---|---|---|---|
| 18 | (1-{4-[1-(3-Fluoro-phenyl)-1H-pyrazol-4-ylmethyl]-3,4,5,6-tetrahydro-2H-[1,2']bipyrazinyl-3'-yl}-piperidin-4-yl)-methanol hydrochloride | 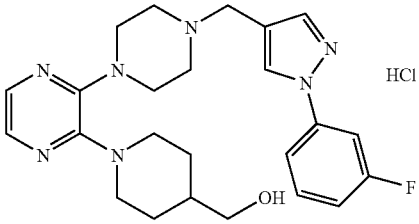 | 452.5 |
| 19 | (1-{4-[1-(3-Fluoro-phenyl)-3-methyl-1H-pyrazol-4-ylmethyl]-3,4,5,6-tetrahydro-2H-[1,2']bipyrazinyl-3'-yl}-piperidin-4-yl)-methanol hydrochloride | 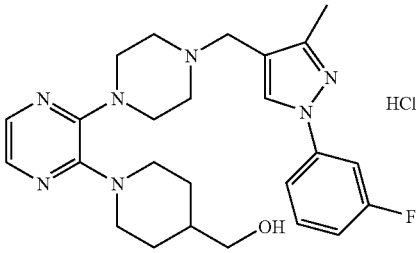 | 466.2 |
| 20 * *** | 2-{4-[3'-(4-Methyl-piperidin-1-yl)-2,3,5,6-tetrahydro-[1,2']bipyrazinyl-4-ylmethyl]-pyrazol-1-yl}-ethanol hydrochloride | 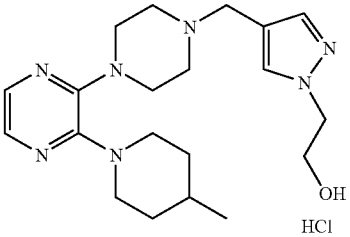 | 386.2 |
| 21 * *** | {1-[4-(3-Methyl-1-phenyl-1H-pyrazol-4-ylmethyl)-3,4,5,6-tetrahydro-2H-[1,2']bipyrazinyl-3'-yl]-piperidin-4-yl}-acetonitrile hydrochloride | 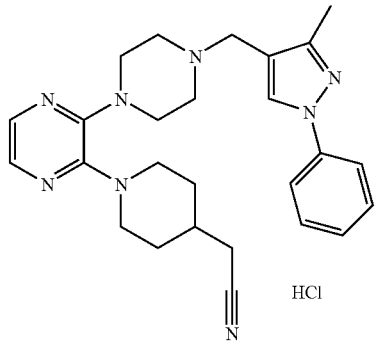 | 457.2 |
| 22 | (1-{4-[1-(2-Fluoro-phenyl)-1H-pyrazol-4-ylmethyl]-3,4,5,6-tetrahydro-2H-[1,2']bipyrazinyl-3'-yl}-piperidin-4-yl)-methanol hydrochloride | 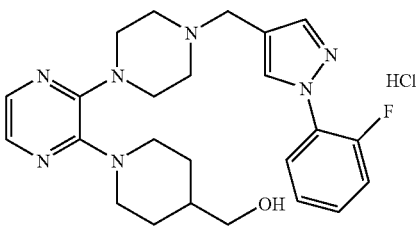 | 452.2 |

| Example | Compound | Structure | MS (ES) [M + H] |
|---|---|---|---|
| 23 | (1-{4-[1-(2,5-Difluoro-phenyl)-1H-pyrazol-4-ylmethyl]-3,4,5,6-tetrahydro-2H-[1,2']bipyrazinyl-3'-yl}-piperidin-4-yl)-methanol hydrochloride | 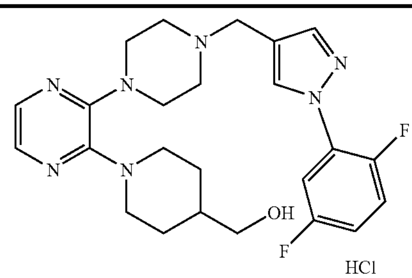 | 470.17 |

\* Reaction is carried out under conventional heating in a sealed tube rather than under microwave condition as in Example 1.
\*\* Appropriate substituted piperidine is used as its HCl salt and diisopropylethylamine is added to prevent decomposition.
\*\*\* Appropriate solvent such as 1,4-dioxane or pyridine is used.

EXAMPLE 24

{3'-[4-(1-Ethyl-1H-pyrazol-4-ylmethyl)-piperazin-1-yl]-3,4,5,6-tetrahydro-2H-[1,2']bipyridinyl-4-yl}-methanol hydrochloride

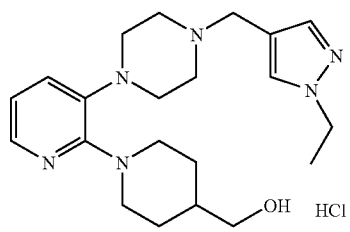

To a solution of (3'-piperazin-1-yl-3,4,5,6-tetrahydro-2H-[1,2']bipyridinyl-4-yl)-methanol (0.145 g, 0.524 mmol, 1 eq) and 1-ethyl-1H-pyrazole-4-carbaldehyde (97.69 mg, 0.787 mmol, 1.5 eq) in 1,2-dichloroethane (10 mL) add sodium triacetoxyborohydride (166.79 mg, 0.787 mmol, 1.5 eq) in one portion as a solid. Stir the mixture at room temperature under nitrogen for 20 hr. Add 2 M aqueous sodium hydroxide solution (20 ml) and DCM (20 ml). Separate using a phase separator and extract the aqueous layer with DCM (10 ml). Concentrate the combined organic extracts and purify by high pH reverse phase HPLC. Dissolve this material (120 mg, 0.31 mmol) in the minimum quantity of 50% aqueous acetonitrile. Add 2 M aqueous hydrogen chloride (155 µL, 0.31 mmol) and lyophilize to give the title compound (127 mg, 58%). MS (m/z): 385.2 (M+1).

The following compounds are prepared essentially by the method of Example 24 using the appropriate 1-(2-(substituted-piperidin-1-yl)pyridin-3-yl) piperazine or 2-(substituted-piperidin-1-yl)-3-(piperazin-1-yl)pyrazine, and substituted-1H-pyrazole-4-carbaldehyde.

| Example | Compound | Structure | MS (ES) [M + H] |
|---|---|---|---|
| 25 | 3'-(4-Methyl-piperidin-1-yl)-4-(1-methyl-1H-pyrazol-4-ylmethyl)-3,4,5,6-tetrahydro-2H-[1,2']bipyrazinyl hydrochloride | 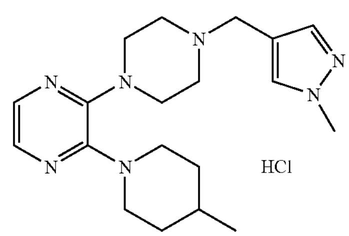 | 356.2 |
| 26 | {3'-[4-(1-Ethyl-3-methyl-1H-pyrazol-4-ylmethyl)-piperazin-1-yl]-3,4,5,6-tetrahydro-2H-[1,2']bipyridinyl-4-yl}-methanol hydrochloride | 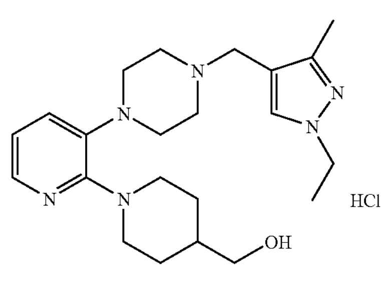 | 399.3 |

-continued

| Example | Compound | Structure | MS (ES) [M + H] |
|---|---|---|---|
| 27 | {3'-[4-(3,5-Dimethyl-1-pyridin-2-yl-1H-pyrazol-4-ylmethyl)-piperazin-1-yl]-3,4,5,6-tetrahydro-2H-[1,2']bipyridinyl-4-yl}-methanol hydrochloride | 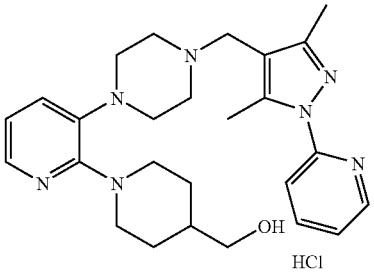 | 462.3 |
| 28 | {3'-[4-(3-Ethyl-1-phenyl-1H-pyrazol-4-ylmethyl)-piperazin-1-yl]-3,4,5,6-tetrahydro-2H-[1,2']bipyridinyl-4-yl}-methanol hydrochloride | 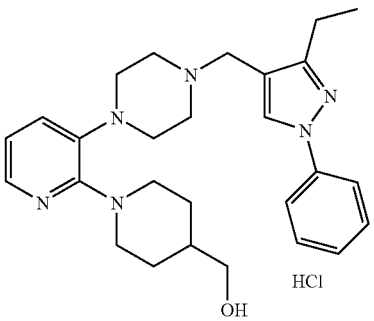 | 461.2 |
| 29 | {1-[4-(1-Ethyl-1H-pyrazol-4-ylmethyl)-3,4,5,6-tetrahydro-2H-[1,2']bipyrazinyl-3'-yl]-piperidin-4-yl}-methanol hydrochloride | 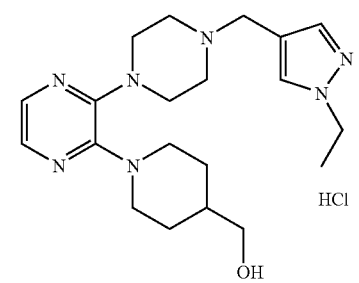 | 386.3 |
| 30 | 1-[4-(1,3-Dimethyl-1H-pyrazol-4-ylmethyl)-3,4,5,6-tetrahydro-2H-[1,2']bipyrazinyl-3'-yl]-piperidin-4-yl}-methanol hydrochloride | 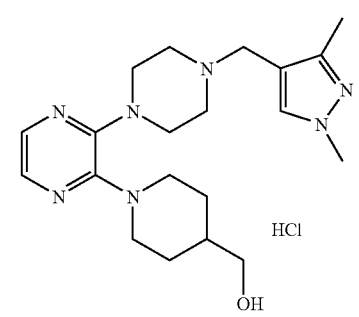 | 386.3 |
| 31 | {1-[4-(1-Benzyl-3,5-dimethyl-1H-pyrazol-4-ylmethyl)-3,4,5,6-tetrahydro-2H-[1,2']bipyrazinyl-3'-yl]piperidin-4-yl}methanol hydrochloride | 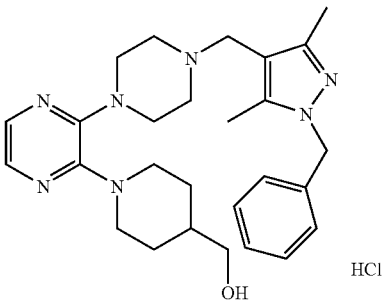 | 476.3 |

| Example | Compound | Structure | MS (ES) [M + H] |
|---|---|---|---|
| 32 | (1-{4-[1-(4-Fluoro-phenyl)-5-methyl-1H-pyrazol-4-ylmethyl]-3,4,5,6-tetrahydro-2H-[1,2']bipyrazinyl-3'-yl}-piperidin-4-yl)-methanol hydrochloride | 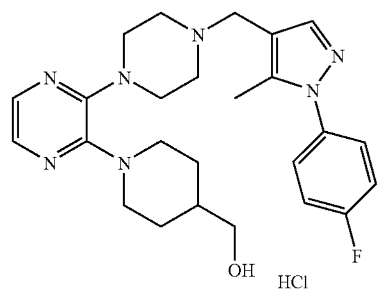 | 466.3 |
| 33 | {1-[4-(1-Ethyl-5-methyl-1H-pyrazol-4-ylmethyl)-3,4,5,6-tetrahydro-2H-[1,2']bipyrazinyl-3'-yl]-piperidin-4-yl}-methanol hydrochloride | 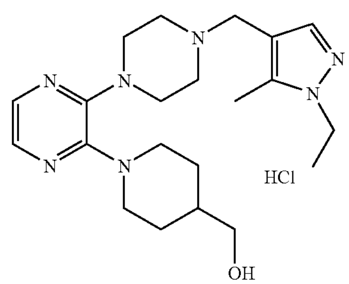 | 400.3 |
| 34 | {1-[4-(1,3,5-Trimethyl-1H-pyrazol-4-ylmethyl)-3,4,5,6-tetrahydro-2H-[1,2']bipyrazinyl-3'-yl]-piperidin-4-yl}-methanol hydrochloride | 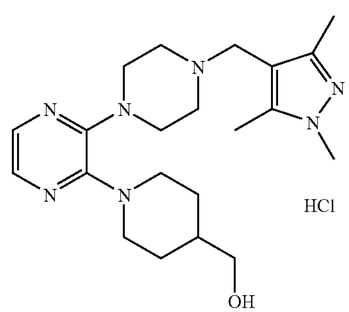 | 400.3 |
| 35 | {1-[4-(1-Methyl-1H-pyrazol-4-ylmethyl)-3,4,5,6-tetrahydro-2H-[1,2']bipyrazinyl-3'-yl]-piperidin-4-yl}-methanol hydrochloride | 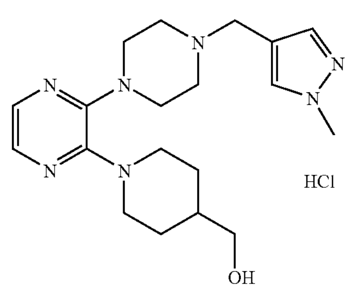 | 372.3 |
| 36 | 2-{4-[3'-(4-Hydroxymethyl-piperidin-1-yl)-2,3,5,6-tetrahydro-[1,2']bipyrazinyl-4-ylmethyl]-pyrazol-1-yl}-ethanol hydrochloride | 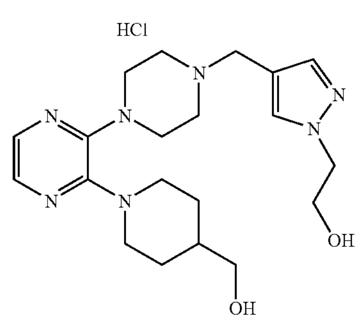 | 402.2 |

-continued

| Example | Compound | Structure | MS (ES) [M + H] |
|---|---|---|---|
| 37 | {1-[4-(3-Methyl-1-phenyl-1H-pyrazol-4-ylmethyl)-3,4,5,6-tetrahydro-2H-[1,2']bipyrazinyl-3'-yl]-piperidin-4-yl}-methanol hydrochloride | 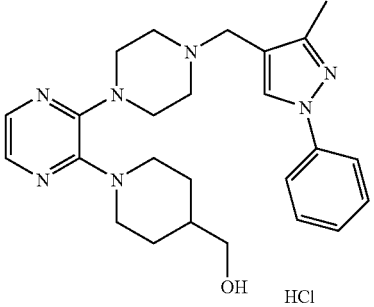 | 448.4 |
| 38 | 2-[4-(3'-Piperidin-1-yl-2,3,5,6-tetrahydro-[1,2']bipyrazinyl-4-ylmethyl)-pyrazol-1-yl]-ethanol hydrochloride | 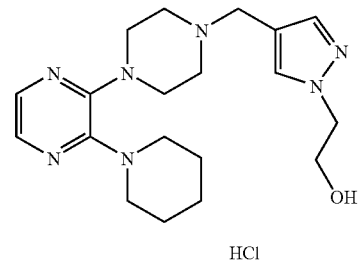 | 372.2 |
| 39 | {1-[4-(5-Methyl-1-phenyl-1H-pyrazol-4-ylmethyl)-3,4,5,6-tetrahydro-2H-[1,2']bipyrazinyl-3'-yl]-piperidin-4-yl}-methanol hydrochloride | 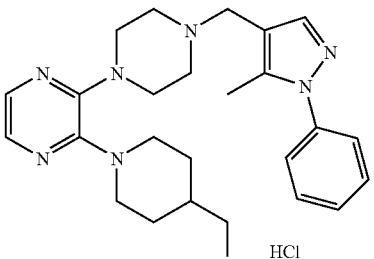 | 448.2 |
| 40 | {1-[4-(3,5-Dimethyl-1-phenyl-1H-pyrazol-4-ylmethyl)-3,4,5,6-tetrahydro-2H-[1,2']bipyrazinyl-3'-yl]-piperidin-4-yl}-methanol hydrochloride | 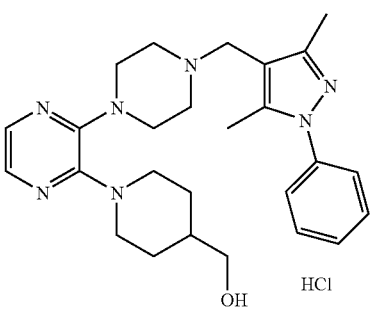 | 462.2 |
| 41 | {1-[4-(3,5-Dimethyl-1-pyridin-2-yl-1H-pyrazol-4-ylmethyl)-3,4,5,6-tetrahydro-2H-[1,2']bipyrazinyl-3'-yl]-piperidin-4-yl}-methanol hydrochloride | 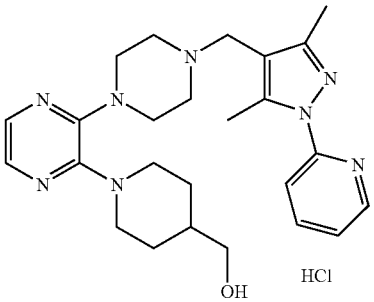 | 463.2 |

| Example | Compound | Structure | MS (ES) [M + H] |
|---|---|---|---|
| 42 | 1-[4-(5-Methyl-1-phenyl-1H-pyrazol-4-ylmethyl)-3,4,5,6-tetrahydro-2H-[1,2']bipyrazinyl-3'-yl]-piperidin-4-ol hydrochloride | 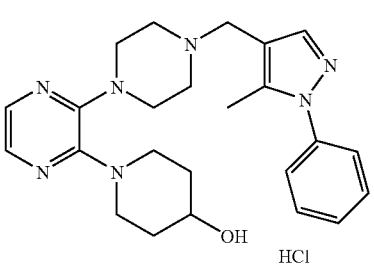 | 434.2 |
| 43 | 1-[4-(3-Methyl-1-phenyl-1H-pyrazol-4-ylmethyl)-3,4,5,6-tetrahydro-2H-[1,2']bipyrazinyl-3'-yl]-piperidin-4-ol hydrochloride | 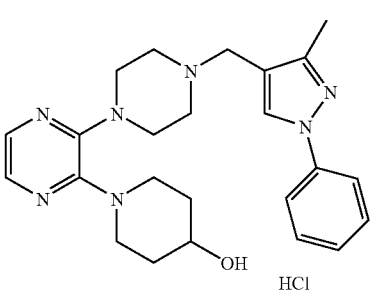 | 434.2 |
| 44 | {1-[4-(5-Methyl-1-pyridin-2-yl-1H-pyrazol-4-ylmethyl)-3,4,5,6-tetrahydro-2H-[1,2']bipyrazinyl-3'-yl]-piperidin-4-yl}-methanol hydrochloride | 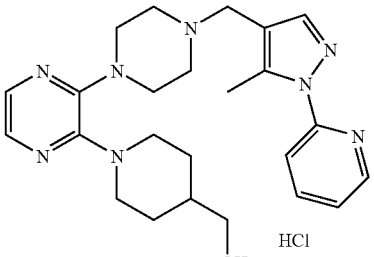 | 449.2 |
| 45 | 1-[4-(5-Methyl-1-pyridin-2-yl-1H-pyrazol-4-ylmethyl)-3,4,5,6-tetrahydro-2H-[1,2']bipyrazinyl-3'-yl]-piperidin-4-ol hydrochloride | 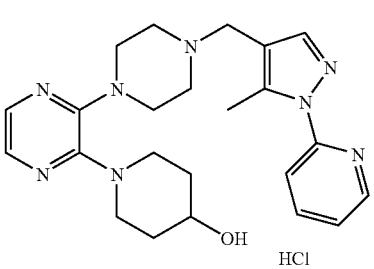 | 435.2 |
| 46 | 4-(5-Methyl-1-phenyl-1H-pyrazol-4-ylmethyl)-3'-piperidin-1-yl-3,4,5,6-tetrahydro-2H-[1,2']bipyrazinyl hydrochloride | 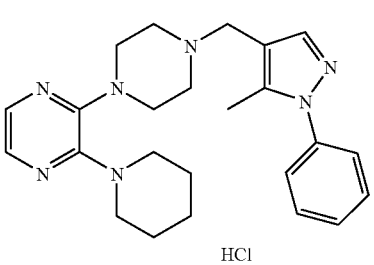 | 418.2 |

-continued

| Example | Compound | Structure | MS (ES) [M + H] |
|---|---|---|---|
| 47 | 4-(3,5-Dimethyl-1-pyridin-2-yl-1H-pyrazol-4-ylmethyl)-3'-(4-fluoro-piperidin-1-yl)-3,4,5,6-tetrahydro-2H-[1,2']bipyrazinyl hydrochloride | 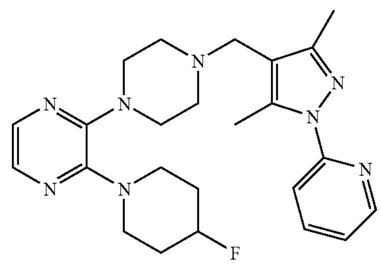 | 451.2 |
| 48 | {1-[4-(5-Chloro-3-methyl-1-phenyl-1H-pyrazol-4-ylmethyl)-3,4,5,6-tetrahydro-2H-[1,2']bipyrazinyl-3'-yl]-piperidin-4-yl}-methanol hydrochloride | 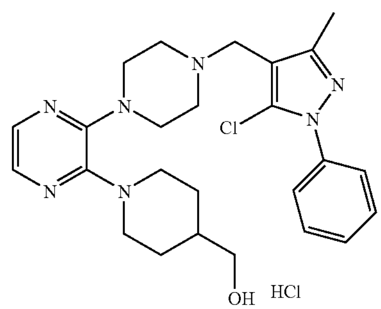 | 482.2 |
| 49 | 3'-(4-Fluoro-piperidin-1-yl)-4-(5-methyl-1-pyridin-2-yl-1H-pyrazol-4-ylmethyl)-3,4,5,6-tetrahydro-2H-[1,2']bipyrazinyl hydrochloride | 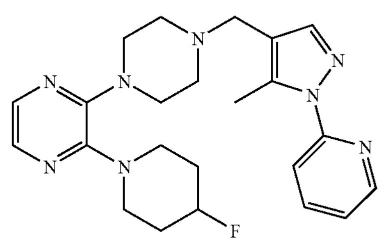 | 437.2 |
| 50 | {1-[4-(1-Ethyl-3,5-dimethyl-1H-pyrazol-4-ylmethyl)-3,4,5,6-tetrahydro-2H-[1,2']bipyrazinyl-3'-yl]-piperidin-4-yl}-methanol hydrochloride | 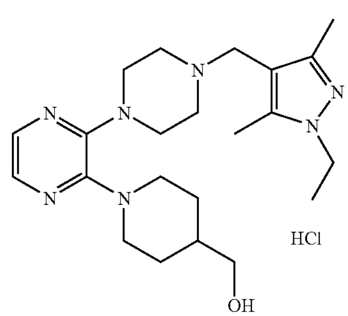 | 414.2 |

EXAMPLE 51

{1-[4-(1,5-Dimethyl-1H-pyrazol-4-ylmethyl)-3,4,5,6-tetrahydro-2H-[1,2']bipyrazinyl-3'-yl]-piperidin-4-yl}-acetonitrile hydrochloride

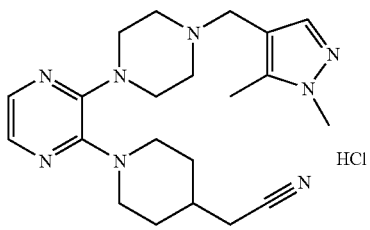

Add sodium cyanide (78.46 mg, 1.60 mmol, 2.4 eq) to a solution of toluene-4-sulfonic acid 1-[4-(1,5-dimethyl-1H-pyrazol-4-ylmethyl)-3,4,5,6-tetrahydro-2H-[1,2']bipyrazinyl-3'-yl]-piperidin-4-ylmethyl ester (0.36 g, 0.667 mmol, 1 eq) in dimethyl sulfoxide (5 mL). Heat the solution to 50° C. with stirring for 5.75 hr. and then cool to room temperature. Add water (20 mL) and extract the aqueous layer three times with DCM (20 mL). Combine the organic extracts, dry over magnesium sulphate, filter and concentrate. Purify by flash chromatography on a 40 g silica gel column, eluting with a gradient of 2-10% methanol in DCM. Further purify by high pH reverse phase HPLC (UV guided). Dissolve this material (148 mg, 0.38 mmol) in the minimum quantity of 50% aqueous acetonitrile. Add 2M aqueous hydrogen chloride (190 μL, 0.38 mmol) and lyophilize to give {1-[4-(1,5-dimethyl-1H-pyrazol-4-ylmethyl)-3,4,5,6-tetrahydro-2H-[1,2']bipyrazinyl-3'-yl]-piperidin-4-yl}-acetonitrile hydrochloride (166 mg, 58%). MS (m/z): 395.2 (M+1).

EXAMPLE 52

3'-[4-(1-Ethyl-5-methyl-1H-pyrazol-4-ylmethyl)-piperazin-1-yl]-3,4,5,6-tetrahydro-2H-[1,2]bipyridinyl-4-ol dihydrochloride

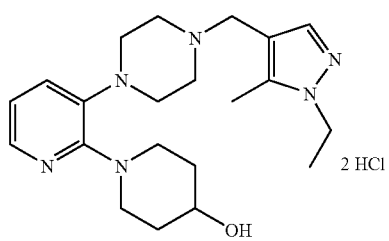

4-(2-Chloro-pyridin-3-yl)-piperazine-1-carboxylic acid tert-butyl ester

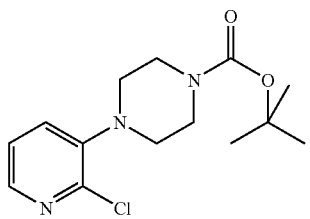

Stir 3-bromo-2-chloropyridine (460 g, 2.39 mole) in toluene (2.3 liters). Add N-t-butoxycarbonyl piperazine (445.2 g, 2.39 mole) and purge with nitrogen for 15 min. Add Tris (dibenzylideneacetone) dipalladium (0) (43.78 g, 47.8 mmole) and 4,5-bis(diphenylphosphino)-9,9-dimethylxanthene (82.99 g, 143 mmols) and purge with nitrogen for 15 min. Transfer the mixture to a one-gallon autoclave and maintain under nitrogen. Add sodium t-butoxide (252.69 g, 2.63 mole) (observing a slight exotherm).

Pressurize the autoclave with nitrogen to 40 psi (275.6 KPa) and release the pressure, three times and then pressurize with nitrogen to 20-40 psi (137.8-275.6 Kpa) and quickly heat the mixture to 110° C. The temperature rises by exothermic reaction to about 113° C. Stir the reaction for 2.75 hours at 110° C. and 20-40 psi (137.8-275.6 Kpa) under nitrogen. Cool the mixture is cooled and test for reaction completion (HPLC analysis). Filter the mixture over glass fiber paper and wash with toluene.

Transfer the filtered mixture to a separatory flask and extract with water (2 liters). Extract the aqueous phase twice with ethyl acetate (3 L, then 2 L). Wash the combined organic phases twice with 15% NaCl solution (4 L, then 2 L). Stir the organics for 30 min. with sodium sulfate and decolorizing carbon (100 g). Filter the mixture and evaporate the filtrate on a rotary evaporator to obtain a dark oil (831 g).

Dissolve the above crude product in ethyl acetate (3 L) and load onto a sintered glass funnel packed with silica gel (6 Kg, packed using heptane). Wash the column with 95% heptane: 5% ethyl acetate (8 L), then elute with 70% heptane: 30% ethyl acetate, collecting fraction containing the crude product. Further purify the combined product containing fractions by silica gel chromatography with 5% methyl t-butyl ether in DCM to give 4-(2-chloro-pyridin-3-yl)-piperazine-1-carboxylic acid t-butyl ester (331 g, 46.5%) as a yellow solid. $^1$H NMR 500 MHz (CDCl$_3$) δ 8.078 (dd, J=3.2 Hz, 1H), 7.30 (dd, J=6.5 Hz, 1H), 7.201 (m, 1H), 3.616 (m, 4H), 3.018 (m, 4H), 1.485 (s, 9H).

tert-Butyl 4-(2-(4-hydroxypiperidin-1-yl)pyridin-3-yl)piperazine-1-carboxylate

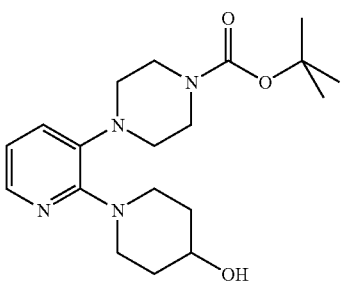

Equip a 2 L flask with a stirrer, thermocouple, and nitrogen line for subsurface addition and purge with under nitrogen atmosphere for 30 min. Add 4-(2-chloro-pyridin-3-yl)-piperazine-1-carboxylic acid t-butyl ester (100 g, 0.336 mole), 4-hydroxypiperidine (37.36 g, 0.369 mol), sodium t-butoxide (80.68 g, 0.839 mol), and acetato (2'-di-t-butylphosphino-1,1'-biphenyl-2-yl)palladium (II) (2.33 g. 5.04 mmol). The mixture of solids is placed under nitrogen atmosphere for 15 min. In a separate flask, nitrogen is bubbled through toluene (933 mL) for 30 min. Add the toluene to the mixture of solids and stir for 28 hr., bubbling nitrogen slowly through the reaction mixture and controlling the temperature between 16 to 20° C. with a water bath. Add water (1 L) drop-wise, keeping the temperature below 25° C. Separate the phases and extract the aqueous layer with toluene (500 mL). Combine the organics and wash twice with 15% aqueous NaCl. Evaporate the organic phase on a rotary evaporator to obtain an oil. Add toluene (250 mL) and evaporate two times to provide 127.7 g of oil. Dissolve the oil in ethyl acetate (255 mL in 2 volumes) and heat to 65-70° C. Add heptane (1277 ml in 10 volumes) at 65-70° C. Allow the solution to cool to ambient temperature and let stand for 16 to 18 hr. Cool the yellow mixture to 0-5° C. for 1 hr. and then filter. Wash the solids with a solution of 20% ethyl acetate in heptane at 0-5° C. Dry the solid at 45 to 50° C. in a vacuum oven to provide t-butyl 4-(2-(4-hydroxypiperidin-1-yl)pyridin-3-yl)piperazine-1-carboxylate (66.6 g, 54.7%). $^1$H NMR 500 MHz (CDCl$_3$) δ 7.958 (dd, J=3.3 Hz, 1H), 7.10 (d, J=7.1 Hz, 1H), 6.834 (m, 1H), 4.01 (d, J=3.2, 2H), 3.865 (m, 1H), 3.578 (m, 4H), 3.041 (m, 4H), 2.945 (m, 2H), 1.643 (m, 2H), 1.487 (s, 9H).

1-(3-(piperazin-1-yl)pyridin-2-yl)piperidin-4-ol dihydrochloride

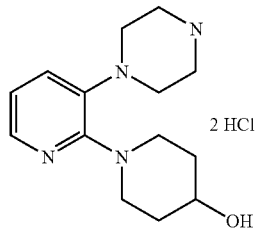

In an ice bath cooled 2 L flask, add HCl gas to methanol (900 ml) to prepare a 7.31 M solution, keeping the temperature below 20° C.

Add t-Butyl 4-(2-(4-hydroxypiperidin-1-yl)pyridin-3-yl)piperazine-1-carboxylate (306.5 g, 0.846 mol) to a 12-liter flask, followed by methanol (613 ml) and toluene (3.06 L). Stir the mixture to give a solution and then add the methanolic HCl solution (579 mL). Heat the solution to 35° C. for 2 hr. followed by 4 hr. at ambient temperature. Filter off the resulting crystalline product, wash the crystals with toluene, and then dry in a vacuum oven at 40-45° C. to provide 1-(3-(piperazin-1-yl)pyridin-2-yl)piperidin-4-ol dihydrochloride as a crystalline solid (283.5 g, 99.47%). $^1$H NMR 300 MHz (DMSO) δ 9.624 (bs, 2H) 7.890 (dd, J=6.4 Hz, 1H), 7.633 (d, J=7.75 Hz, 1H), 7.137 (m, 1H), 3.916 (bm, 2H), 3.727 (bm, 1H), 3.236 (bs, 9H), 1.877 (bm, 2H), 1.515 (bm, 2H).

1-(3-(piperazin-1-yl)pyridin-2-yl)piperidin-4-ol

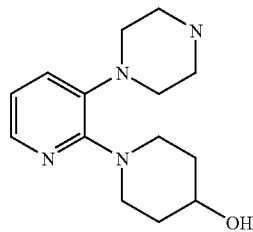

Dissolve 1-(3-(piperazin-1-yl)pyridin-2-yl)piperidin-4-ol dihydrochloride (281.0, 0.838 mol) in saturated aqueous sodium chloride solution (2.45 liters). Add 2 M NaOH (~1 L) to bring the pH to 11.3. Extract the mixture three times with DCM (3×2.04 L). Dry the combined organics over sodium sulfate, filter, and evaporate solvent on a rotary evaporator with a nitrogen bleed to obtain a foam. When the foam is stable, further dry the material for 2 to 3 hr. at 50° C. under vacuum to provide 1-(3-(piperazin-1-yl)pyridin-2-yl)piperidin-4-ol (207.5 g, 94.1%). $^1$H NMR 300 MHz (CDCl$_3$) δ 7.923 (dd, J=3.1 Hz, 1H), 7.10 (d, J=6.3 Hz, 1H), 6.815 (m, 1H), 4.040 (m, 2H), 3.840 (m, 1H), 3.048 (bs, 8H), 2.898 (m, 2H), 2.028 (m, 2H), 1.862 (s, 2H ??), 1.634 (m, 2H).

3'-[4-(1-Ethyl-5-methyl-1H-pyrazol-4-ylmethyl)-piperazin-1-yl]-3,4,5,6-tetrahydro-2H-[1,2']bipyridinyl-4-ol

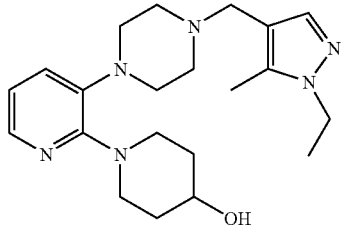

Dissolve 1-(3-(piperazin-1-yl)pyridin-2-yl)piperidin-4-ol (207 g, 0.789 mol) and 1-ethyl-5-methyl-1H-pyrazole-4-carbaldehyde (130.8 g, 0.947 mol) in dichloroethane (4.55 L). Cool to −5° C. and begin to add sodium triacetoxyborohydride (334.5 g, 1.578 mol) portion-wise, maintaining the temperature below about 5° C. Remove the ice bath and allow the reaction to warm to 10° C. over about 1 hr. Warm the reaction to 18-20° C. and stir for 3 hr.

Cool the reaction mixture to 15° C. and add 2N NaOH (2 L). Separate the phases and extract the aqueous layers twice with DCM (2×1.3 L). Filter the combined organic layers over glass-fiber paper. Extract the organics with 1 N HCl (1×2.5 L once, 2×1 L). To the combined aqueous layers which contain the product, add 50% NaOH (400 mL) to bring the pH to 11.6. Extract the resulting milky aqueous layer with DCM (1×3 L, 2×1.5 L). Dry the combined organics over sodium sulfate. Add decolorizing carbon (G-60, 44 g) and stir the mixture at ambient temperature for 20 min. Filtered over glass-fiber paper, rinse with DCM (1 L), and evaporate the solvents to provide 3'-[4-(1-ethyl-5-methyl-1H-pyrazol-4-ylmethyl)- piperazin-1-yl]-3,4,5,6-tetrahydro-2H-[1,2]bipyridinyl-4-ol as an oil (330 g, 109%). $^1$H NMR 300 MHz (CDCl$_3$) (E29-H70357-031) δ 7.87 (dd, J=3.3 Hz, 1H), 7.37 (s, 1H) 7.05 (dd, J=6.26 Hz, 1H), 6.77 (m, 1H), 4.065 (q, J=7.35 Hz, 2H), 3.99 (bm, 2H), 3.802 (bm, 1H), 3.365 (s, 2H), 2.658 (bm, 2H), 2.551 (bm, 3H), 2.236 (s, 3H), 1.985 (bm, 2H), 1.615 (bm, 2H), 1.381 (t, J=7.26 Hz, 3H).

3'-[4-(1-Ethyl-5-methyl-1H-pyrazol-4-ylmethyl)-piperazin-1-yl]-3,4,5,6-tetrahydro-2H-[1,2']bipyridinyl-4-ol dihydrochloride Dissolve 3'-[4-(1-Ethyl-5-methyl-1H-pyrazol-4-ylmethyl)-piperazin-1-yl]-3,4,5,6-tetrahydro-2H-[1,2]bipyridinyl-4-ol (415 g, 1.079 mol)) in ethanol (5.5 liters) and methyl t-butyl ether (6.23 liters). Stir the solution under a nitrogen atmosphere and heat to 50-55° C. Add 2.96 M HCl solution in ethanol (0.729 L) at 50-55° C. over 50 min. Allow the mixture to cool to about 40.1° C. over 90 min. Cool the mixture to 20° C. over 20 min., and then stir at 20° C. for 30 min. Filter the mixture and wash with methyl t-butyl ether (3×500 mL). Dry the solid in a vacuum oven at 50-55° C. under vacuum with a slight nitrogen sweep for 24 hr. to provide 3'-[4-(1-ethyl-5-methyl-1H-pyrazol-4-ylmethyl)-piperazin-1-yl]-3,4,5,6-tetrahydro-2H-[1,2]bipyridinyl-4-ol dihydrochloride (416 g, 84.3%). $^1$H NMR 500 MHz (CD$_3$OD) δ 7.89 (dd, J=6.0 Hz, 2H), 7.828 (s, 1H), 7.275 (dd, J=6.0 Hz, 1H), 4.86 (CD3OH), 4.385 (s, 2H), 4.220 (q, J=7.1 Hz, 2H), 4.04 (bm, 2H), 3.976 (bm, 1H), 3.70 (bm, 4H), 3.511 (bm, 2H), 3.410 (bt, 2H), 3.145 (t, J=8.1, 2H), 2.467 (s, 3H), 2.082 (bm, 2H), 1.716 (bm, 2H), 1.416 (t, J=7.5 Hz, 3H). Chloride analysis is obtained by ICP/MS (15.6%).

The 5-HT$_7$ receptor antagonists of the present invention are relatively selective for the 5-HT$_7$ receptor. The compounds of the present invention are particularly relatively selective for the 5-HT$_7$ receptor in comparison to other 5-HT receptor subtypes and specifically the 5-HT$_{1A}$, 5-HT$_{1B}$ and 5-HT$_{1D}$ receptors. This selectivity is demonstrated in the following receptor binding assays and receptor antagonist activity assays.

Membrane Preparation:

Membranes for affinity and antagonist activity assays are prepared essentially as follows. AV-12 cells, stably expressing the 5-HT$_7$ receptor, are grown as a monolayer in 5×T-150 flasks in DMEM/F12 (3:1) 5% FBS, 20 mM HEPES, 400 mg/mL geneticin, 50 mg/mL tobramycin. After growing to 90% confluence the media is removed and replaced with Hybritech media containing 2% horse serum, 100 mg/mL dextran sulfate, 1 mg/mL nucellin, 1 mg/mL human transferrin (partially iron saturated), 50 mg/mL tobramycin, 20 mM HEPES, 100 mg/mL geneticin, 0.04% pluronic F68. (Hybritech media is a low calcium modified DMEM/F12 media for supporting cell growth in suspension having the following formula: biotin 7.3 mg/L, calcium chloride anhydride 11 mg/L, choline chloride 8.98 mg/L, cupric sulfate 5H$_2$O 3.75 mg/L, D glucose (dextrose) 6.00 g/L, DL lipoic acid thioctic 0.21 mg/L, thanolamine HCL 10 mg/L, ferric nitrate 9*H$_2$O 50 mg/L, ferrous sulfate 7*H$_2$O 0.42 mg/L, folic acid 4 mg/L, glycine 30 mg/L, I inositol 12.6 mg/L, L alanine 8.9 mg/L, L arginine HCL 211 mg/L, L asparagine H$_2$O 15 mg/L, L aspartic acid 13.3 mg/L, L cystine 2*HCl 62.6 mg/L, L glutamic acid 7.35 mg/L, L glutamine 1.46 g/L, L histidine HCl H$_2$O 42 mg/L, L isoleucine, 105 mg/L, L leucine 105 mg/L, L lysine HCl 146 mg/L, L methionine 30 mg/L, L phenylalanine 66 mg/L, L proline 17.25 mg/L, L serine 42 mg/L, L threonine 95 mg/L, L tryptophan 16 mg/L, L tyrosine disodium salt 104 mg/L, L valine 94 mg/L, magnesium chloride anhydrate 28.64 mg/L, magnesium sulfate anhydrate 48.84 mg/L, niacinamide 4 mg/L, KCl 311.8 mg/L, purescine 2*HCl 0.08 mg/L, pyridoxal HCl 4 mg/L, pyridoxine HCl 30 μg/L, riboflavin 0.4 mg/L, NaCl 5.50 g/L, sodium hypoxanthine 4.77 mg/L, sodium pantothenate 4 mg/L, sodium phosphate di-basic anhydrate 71.2 mg/L, sodium phosphate mono-basic 62.5 mg/L, sodium pyruvate 220 mg/L, sodium selenite 5.00 μg/L, thiamine HCl 4 mg/L, thymidine 0.73 mg/L, vitamin B-12 0.68 mg/L, zinc sulfate 7*H$_2$O 0.43 mg/L.) The cells are grown overnight to condition the media. The next morning the conditioned media (~150 mL total) is removed and set aside in a sterile container. The cells are trypsinized and collected in the conditioned media. Fresh suspension media is added to bring the total volume to 500 mL and a cell density of 5×10$^5$ cells/mL. The suspension culture volume is repeatedly increased over the next 3 weeks to the desired volume and density until harvest (approx. 3.5–4.0×10$^6$ cells per mL targeted cell density). Cells are harvested by centrifugation at 1,500 g at 4° C. for 30 min. The supernatant is decanted and the cell pellets are resuspended in ice-cold phosphate buffered saline (PBS). The cell suspension is aliquoted into 50 mL centrifuge tubes and centrifuged at 1,500 g at 4° C. for 15 min. The supernatant is removed, the pellets are weighed, and then frozen on dry ice.

To prepare membranes, the above pellets are resuspended in ice-cold Tris buffer (20 mM Tris HCl, pH 7.4 at 23° C., 5 mM EDTA) and homogenized with a Wheaton tissue grinder. The lysate is subsequently centrifuged at 200×g for 5 min. at 4° C. to pellet large fragments which are discarded. The supernatant is collected and centrifuged at 40,000×g for 60 min. at 4° C. The resulting pellet is resuspended in a final buffer containing 50 mM Tris HCl and 0.5 mM EDTA, pH 7.4. Membrane preparations are snap-frozen on dry ice and stored at −80° C. Protein concentrations are determined by the method of Bradford. *Anal. Biochem.*, 72:248-254, 1976.

For cAMP functional assays, the 5-HT$_7$-expressing cells from above are grown in 150 cm$^2$ flasks and processed essentially as follows. The media is aspirated from the flasks and cells are washed with 1 mL PBS. The cells are released from the flask surface using enzyme free cell dissociation solution (Specialty media (www.chemicon.com) CAT#S-004-B) and resuspended in complete media. A sample of the cells is counted and the remainder is centrifuged as above for 3 min. The resulting cell pellet is resuspended in PBS at a concentration of 1×10$^6$ cells per mL and used directly in the cAMP assay as described.

5-HT$_7$ Receptor Affinity: Radioligand Binding Assay:

[$^3$H] 5-HT binding is performed using modifications of the assay conditions reported by Kahl et al. (*J. Biomol. Screen*, 2: 33-40 (1997), essentially as follows. Radioligand binding assays are conducted in 96-well microtiter plates, in a total volume of 125 μl containing the following reaction buffer: 50 mM Tris, 10 mM MgCl$_2$, 0.2 mM EDTA, 10 mM pargyline, 0.1% ascorbate, pH 7.4 at room temperature. Competition binding is conducted using eleven test compound concentrations ranging from 0.1 to 10,000 nM, in the presence of 1 nM [$^3$H]5-HT. Unlabeled 5-HT (10 μM) is used to define nonspecific binding. The binding reaction is initiated by addition of 0.15 μg of membrane homogenate (2.31 ng/μL, 65 μL per well) and 0.5 mg of scintillation proximity assay fluoromicrospheres. The reactions are incubated at room temperature for 3 hr. and then counted in a Trilux Microbeta™ scintillation counter to detect receptor-bound radioligand. Binding data are analyzed by computer-assisted 4 parameter fit analysis (ID Business Solutions Ltd, Guildford, Surrey, UK). IC$_{50}$ values are converted to K$_i$ values using the Cheng-Prusoff equation. *Biochem. Pharmacol.*, 22:3099-3108 (1973).

Exemplified compounds are tested essentially as described and found to have $K_i$ values $\leq 50$ nM. The compound of Example 1 is tested essentially as described and is found to have a $K_i$ value of about 16.2 nM.

Affinity for other serotonin receptor subtypes as well as for alpha 1 & 2 adrenergic receptors can readily be determined by modification of the above described radioligand receptor binding assay using membranes derived from cells stably expressing the desired receptor subtype including the $5\text{-}HT_{1A}$, $5\text{-}HT_{1B}$, and $5\text{-}HT_{1D}$ subtypes, as well as the $5\text{-}HT_{2A}$, $5\text{-}HT_{2B}$, $5\text{-}HT_{2C}$, $5\text{-}HT_4$, $5\text{-}HT_7$, and $5\text{-}HT_6$ receptor subtypes. The selectivity ratio of $K_{i\text{-}x}/K_{i\text{-}5HT7}$, where $K_{i\text{-}x}$ is the $K_i$ for the receptor being compared, is indicative of the relative affinity of a compound for the $5\text{-}HT_7$ receptor. Exemplified compounds are tested and found to have selectivity ratios against other serotonergic receptors of $\geq 4$ and against andronergic receptors of $\geq 4$. The compound of Example 1 is tested essentially as described and is found to have the following selectivity profile:

| Receptor | Ex. 1 $K_i$ (nM) |
| --- | --- |
| $5\text{-}HT_{1A}$ | 213 |
| $5\text{-}HT_{1B}$ | >3580 |
| $5\text{-}HT_{1D}$ | 1840 |
| $5\text{-}HT_{2A}$ | >7470 |
| $5\text{-}HT_{2B}$ | >6810 |
| $5\text{-}HT_{2C}$ | >8360 |
| $5\text{-}HT_4$ | (not tested) |
| $5\text{-}HT_5$ | 4550 |
| $5\text{-}HT_6$ | >5830 |
| $5\text{-}HT_7$ | 16.2 |
| alpha 1 adrenergic | 1380 |
| alpha 2 adrenergic | >2670 |

Functional Antagonist Assay: Measurement of cAMP Formation:

The $5\text{-}HT_7$ receptor is functionally coupled to a G-protein as measured by the ability of serotonin and serotonergic drugs to stimulate cAMP production in CHO cells transfected with the $5\text{-}HT_7$ receptor. (Ruat, et al., *Proceedings of the National Academy of Sciences (USA)*, 90:8547-8551, 1993.) Accordingly, functional receptor activity can be measured by measuring adenylate cyclase activity using a commercially available cell-based, homogeneous, time resolved fluorescence assay kit, as for example the kit produced by Cisbio-US, Inc. (Bedford, Mass.). Essentially, and using the protocol and reagents provided by the manufacturer, approximately 20,000 human $5\text{-}HT_7$ receptor-expressing AV-12 cells (as described above) are used with test compound dose concentrations in the range described for the binding assay. EC-90 dose-response curves for 5-HT are measured in parallel to demonstrate competitive antagonism. A cAMP standard curve is also run in every experiment. After the assay plates are read in an Envision™ instrument (Perkin-Elmer, Wellesley Mass.), the data are normalized to the standard curve and converted to percent inhibition for data analysis as described above for the receptor binding assay results. The $K_b$ (nM) is calculated as a measure of the antagonist potency of the compound. Preferred compounds are those having percent inhibition >75%. Still other preferred compounds are those having $K_b$<50 nM. The compound of Example 1 is tested essentially as described and is found to be a full antagonist with a $K_b$ value of about 2.97 nM (inhibition=about 108%).

Animal Model of Dural Plasma Protein Extravasation (PPE).

The dural plasma protein extravasation model is an established model for migraine. The ability of a test compound to reduce extravasation of plasma proteins into the dura under assay conditions is considered indicative of the compound's ability to reduce or prevent the dural inflammation thought to be symptomatic of migraine. (see Johnson, K. W., et al., *Neuroreport*, 8 (1997) 2237-2240.)

To assay compounds for their ability to reduce or prevent dural plasma protein extravasation, male Harlan Sprague-Dawley rats (250-350 g) are anesthetized with sodium pentobarbital (65 mg/kg, i.p.) and placed in a stereotaxic frame (David Kopf Instruments) with the incisor bar set at −2.5 mm. Following a midline sagital scalp incision, 2 pairs of bilateral holes are drilled through the skull (3.2 mm posterially, 1.8 and 3.8 mm laterally, all coordinates referenced to bregma). Pairs of stainless steel stimulating electrodes, insulated except at the tips (Rhodes Medical Systems, Inc.), are lowered through the holes in both hemispheres to a depth of 9.2 mm.

Test compound is administered intravenously (i.v.) to the femoral vein at a dosing volume of 1 mL/kg. Approximately 8 min. post injection, the animals are dosed with Fluorescein isothiocyanate-bovine serum albumin (FITC-BSA) (20 mg/kg, i.v.). The FITC-BSA functions as a marker for protein extravasation. Ten min. post-injection of the test compound, the left trigeminal ganglion is electrically stimulated for 5 min. at a current intensity of 1.0 mA (5 Hz, 5 msec pulse every 200 msec) with a Model S48 Grass Instrument Stimulator with PSIU6 photoelectric isolation unit (Grass-Telefactor).

Alternatively, rats fasted overnight are dosed orally with test compound via gavage at a volume of 2 mL/kg. Approximately 50 min. post dosing, the animals are anesthetized and placed in the stereotaxic frame as described above. The animals are dosed with FITC-BSA (20 mg/kg, i.v.) at 58 min. post-p.o. dosing. Sixty min. post compound dosing, the animals are electrically stimulated as described above.

Five min. following the termination of stimulation, the animals are killed by exsanguination with 40 mL of saline. The top of the skull is removed and the dural membrane samples are removed from both hemispheres, rinsed with water, and spread flat on microscopic slides. Once dried, the tissues are coverslipped with a 70% glycerol/water solution.

The amount of FITC-BSA for each sample is quantified with a fluorescence microscope (Zeiss) equipped with a grating monochromator, a spectrophotometer, and a computer driven stage. Fluorescence measurements are taken at 25 points in a 5×5 grid in 500 μm steps on each dural sample with an excitation wavelength of approximately 490 nm and emission intensity measured at approximately 535 nm. The mean and standard deviation of the 25 measurements are determined.

The extravasation induced by the electrical stimulation of the trigeminal ganglion is an ipsilateral effect (i.e. occurs only on the side of the dura in which the trigeminal ganglion was stimulated). This allows the use of the other (unstimulated) half of the dura as a control. The ratio of the amount of extravasation in the dura from the stimulated side, over the amount of extravasation in the unstimulated side, is calculated. Control animals dosed only with saline, yield a ratio of approximately 2.0. In contrast, a compound which effectively prevented the extravasation in the dura from the stimulated side would yield a ratio of approximately 1.0.

Preferred compounds are those that effectively prevent extravasation. The compound of Example 1 is assayed essentially as described and is found to have an $ID_{100}$ of 0.1 mg/Kg, providing a ratio of about 1.15.

While it is possible to administer compounds employed in the methods of this invention directly without any formulation, the compounds are usually administered in the form of pharmaceutical compositions comprising at least one compound of Formula I, or a pharmaceutically acceptable salt thereof, as an active ingredient and at least one pharmaceutically acceptable carrier, diluent and/or excipient. These compositions can be administered by a variety of routes including oral, sublingual, buccal, intranasal, transdermal, subcutaneous, intravenous, intramuscular, and pulmonary. Such pharmaceutical compositions and processes for preparing them are well known in the art. See, e.g., Remington: The Science and Practice of Pharmacy (University of the Sciences in Philadelphia, ed., 21$^{st}$ ed., Lippincott Williams & Wilkins Co., 2005).

The compositions are preferably formulated in a unit dosage form, each dosage containing from about 0.1 to about 200 mg, more usually about 1.0 to about 30 mg, of the active ingredient. The term "unit dosage form" refers to physically discrete units suitable as unitary dosages for human subjects and other mammals, each unit containing a predetermined quantity of active material calculated to produce the desired therapeutic effect, in association with at least one suitable pharmaceutically acceptable carrier, diluent and/or excipient.

The compounds are generally effective over a wide dosage range. For example, dosages per day will normally fall within the range of about 0.01 to about 30 mg/kg, as for example within the range of about 0.1 to about 15 mg/kg/day, in single or divided dose. However, it will be understood that the amount of the compound actually administered will be determined by a physician, in the light of the relevant circumstances, including the condition to be treated, the chosen route of administration, the actual compound or compounds administered, the age, weight, and response of the individual patient, and the severity of the patient's symptoms, and therefore the above dosage ranges are not intended to limit the scope of the invention in any way. In some instances dosage levels below the above lower limit may be adequate, while in other cases still larger doses may be used.

The type of formulation employed for the administration of the compounds employed in the methods of the present invention may be dictated by the particular compound employed, the type of pharmacokinetic profile desired from the selected route of administration, and the state of the patient.

We claim:

1. A compound of the formula:

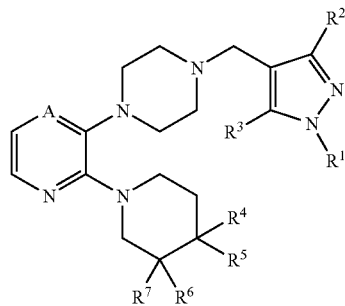

where:

A is —C(H)= or —N=, $R^1$ is a substituent selected from the group consisting of i) hydrogen, ii) methyl, iii) ethyl, iv) hydroxymethyl, v) hydroxyethyl, vi) phenyl optionally substituted with 1 to 3 fluoro groups, vii) benzyl optionally substituted with 1 to 3 fluoro groups, and viii) pyridyl;

$R^2$ is hydrogen, methyl, or ethyl;

$R^3$ is hydrogen, methyl, or chloro;

$R^4$ is selected from the group consisting of i) hydrogen, ii) fluoro, iii) methyl, iv) hydroxy, v) hydroxymethyl, vi) hydroxyethyl, vii) methoxymethyl, viii) cyanomethyl, and ix) methylsulfonylaminomethyl;

$R^5$ is hydrogen or fluoro, provided that when $R^5$ is fluoro, $R^4$ is fluoro;

$R^6$ and $R^7$ are the same and are selected together from the group consisting of hydrogen, methyl, and fluoro, provided that when $R^6$ and $R^7$ are not hydrogen, $R^4$ and $R^5$ are both hydrogen;

or a pharmaceutically acceptable salt thereof.

2. A compound according to claim 1 where $R^1$ is methyl, ethyl, or phenyl optionally substituted with 1 to 2 fluoro groups.

3. A compound according to claim 1 where $R^1$ is methyl, ethyl, or phenyl optionally substituted with 1 to 2 fluoro groups, and $R^4$ is hydroxy, hydroxymethyl, or methoxymethyl.

4. A compound according to claim 1 which is 3'-[4-(1-Ethyl-5-methyl-1H-pyrazol-4-ylmethyl)-piperazin-1-yl]-3,4,5,6-tetrahydro-2H-[1,2]bipyridinyl-4-ol or a pharmaceutically acceptable salt thereof.

5. A pharmaceutical composition comprising a compound according to claim 1 as an active ingredient in association with a pharmaceutically acceptable carrier, diluent or excipient.

6. A method for the treatment of migraine in humans, comprising administering to a human in need of such treatment an effective amount of a compound according to claim 1.

7. A method for the prophylactic treatment of migraine in humans, comprising administering to a human in need of such treatment an effective amount of a compound according to claim 1.

* * * * *